United States Patent [19]

Dawson

[11] Patent Number: 5,589,358
[45] Date of Patent: Dec. 31, 1996

[54] ILEAL BILE ACID TRANSPORTER COMPOSITIONS AND METHODS

[76] Inventor: Paul A. Dawson, 2111 Carriage Way, Chapel Hill, N.C. 27514

[21] Appl. No.: 176,126

[22] Filed: Dec. 29, 1993

[51] Int. Cl.$^6$ .................................................. C12N 15/12
[52] U.S. Cl. .................. 435/69.1; 435/172.3; 435/240.2; 435/252.3; 435/320.1; 536/23.5; 536/24.3; 530/846
[58] Field of Search ............................... 536/23.5, 24.31, 536/24.33, 24.3; 435/6, 172.3, 240.1, 240.2, 252.3, 320.1, 69.1; 530/846

[56] References Cited

U.S. PATENT DOCUMENTS 5,389,543  2/1995  Bunzow et al. ...................... 435/252.3

OTHER PUBLICATIONS

Alves et al., "Bile Acid Transport into Hepatocyte Smooth Endoplasmic Reticulum Vesicles Is Mediated by Microsomal Epoxide Hydrolase, a Membrane Protein Exhibiting Two Distinct Topological Orientations," *J. Biol. Chem.*, 268(27):20148–20155, 1993.
Barnard and Ghishan, "Taurocholate Transport by Human Ilean Brush Border Membrane Vesicles," *Gastroenterology*, 93:925–933, 1987.
Barnes et al., "The Role of Tubular Reabsorption in the Renal Excretion of Bile Acids," *Biochem. J.*, 166:65–73, 1977.
Becker et al., "Characterisation of the ATP–dependent Taurocholate–carrier Protein (gp110) of the Hepatocyte Canalicular Membrane," *Eur. J. Biochem.*, 214:539–548, 1993.
Boyer et al., "Phylogenic and Ontogenic Expression of Hepatocellular Bile Acid Transport," *Proc. Natl. Acad. Sci. USA*, 90:435–438, 1993.
Burckhardt et al., "Photoaffinity Labeling Studies of the Rat Renal Sodium/Bile Salt Cotransport System," *Biochem. Biophys. Res. Commun.*, 143(3):1018–1023, 1987.
Chandler et al., "Transepithelial Transport of Cholyltaurine by Caco-2 Cell Monolayers Is Sodium Dependent," *Am. J. Physiol.*, 264(6):G1118–G1125, 1993.
Galeazzi and Javitt, "Bile Acid Excretion: the Alternate Pathway in the Hamster," *J. Clin. Invest.*, 60:693–701, 1977.
Hagenbuch et al., "Functional Expression Cloning and Characterization of the Hepatocyte Na$^+$/Bile Acid Cotransport System," *Proc. Natl. Acad. Sci. USA*, 88:10629–10633, 1991.
Hofmann et al., "Biological and Medical Aspects of Active Ileal Transport of Bile Acids," *Annals of Medicine*, 23:169–175, 191.
Kramer et al., "Liver-specific Drug Targeting by Coupling to Bile Acids," *J. Biol. Chem.*, 267(26):18598–18604, 1992.
Kramer et al., "Characterization and Chemical Modification of the Na$^+$–dependent Bile–acid Transport System in Brush-border Membrane Vesicles from Rabbit Ileum," *Biochim. Biophys. Acta*, 1111:93–102, 1992.
Kramer et al., "Intestinal Bile Acid Absorption," *J. Biol. Chem.*, 268(24):18035–18046, 1993.
Lack and Weiner, "In vitro Absorption of Bile Salts by Small Intestine of Rats and Guinea Pigs," *Am. J. Physiol.*, 200(2):313–317, 1961.
Lack and Weiner, "Bile Salt Transport Systems," *The Bile Acids*, 2:33–54, 1973.
Lin et al., "Identification of Cytosolic and Microsomal Bile Acid-binding Proteins in Rat Ileal Enterocytes," *J. Biol. Chem.*, 265(25):14986–14995, 1990.
Lin et al., "Timed Photoaffinity Labeling and Characterization of Bile Acid Binding and Transport Proteins in Rat Ileum," *Am. J. Physiol.*, 265 (Gastrointest. Liver Physiol. 28):G56–G62, 1993.
Mullins et al., "Characterization of the Ileal Na$^+$/Bile Sale Co–transporter in Brush Border Membrane Vesicles and Functional Expression in *Xenopus laevis* Oocytes," *Biochem. J.*, 285:785–790, 1992.
Shneider et al., "Physiologic, Immunologic and Molecular Differences in Hepatic and Ileal Sodium-dependent Bile Acid Transport," *Gastroenterology*, 102(4) (Part 2):A888, 1992, abstract only.
Sippel et al., "The Rat Liver Ecto–ATPase Is Also a Canalicular Bile Acid Transport Protein," *J. Biol. Chem.*, 268(3):2083–2091, 1993.
Von Dippe et al., "Na$^+$–dependent Bile Acid Transport by Hepatocytes is Mediated by a Protein Similar to Microsomal Epoxide Hydrolase," *Am. J. Physiol.*, 264 (Gastrointest. Liver Physiol. 27):G528–G534, 1993.
Wilson et al., "Sodium-coupled Taurocholate Transport in the Proximal Convolution of the Rat Kidney in vivo and in vitro," *J. Clin. Invest.*, 67:1141–1150, 1981.
Zimmerli et al., "Multispecificity of Na$^+$–dependent Taurocholate Uptake in Basolateral (Sinusoidal) Rat Liver Plasma Membrane Vesicles," *J. Pharmacol. Exp. Ther.*, 250(1):301–308, 1989.
Gong et al., "Effect of Antiserum to a 99 kDa Polypeptide on the Uptake of Taurocholic Acid by Rat Ileal Brush Border membrane Vesicles," *Biochem. Biophys. Res. Commun.*, 179(1):204–209, 1991.
Sorscher et al., "Conjgated Bile Acid Uptake by Xenopus Laaevis Oocytes Induced by Microinjection with Ileal Poly A$^+$mRNA," *Biochem. Biophys. Res. Commun.*, 186(3):1455–1462, 1992.
Wong et al., "Cloning and Characterization of the Ileal Bile Acid Transporter," *AASLD Abstracts*, 18(4):143A, Pt. 2, 1993.

*Primary Examiner*—Stephen G. Walsh
*Assistant Examiner*—Lorraine Spector
*Attorney, Agent, or Firm*—Arnold, White & Durkee

[57] ABSTRACT

Bile acids are absorbed from the small intestine by an passive and an active mechanism. The active mechanism involves a Na$^+$/bile acid cotransporter. A cDNA encoding the ileal bile acid cotransporter has been isolated and sequenced. The amino acid sequence of the cotransporter protein is also disclosed. The renal bile acid cotransporter is also shown to be identical to the ileal cotransporter. The cotransporter disclosed herein will have use in treatment of hypercholesterolemia, diabetes, heart disease and liver disease. In addition, methods of screening man made and naturally occurring substances for the discovery of new bile acid transport inhibitors and activators and methods of detecting mutations in human ileal/renal bile acid transporter genes are disclosed.

22 Claims, 10 Drawing Sheets

| LIVER | KIDNEY | DUODENUM | JEJUNUM | ILEUM |

KB
9.5 —
7.5 —

4.4 —       ●            ●        IBAT 2.4 —

1.4 —

●  ●  ●  ●  ●    GAPD

FIG.3

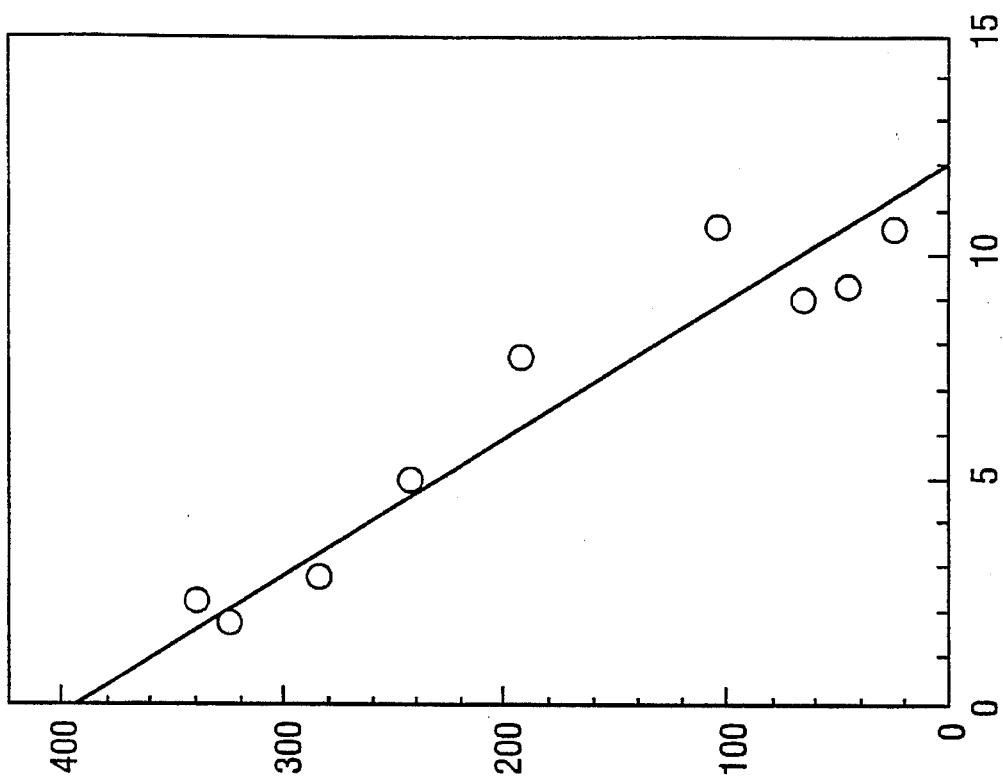
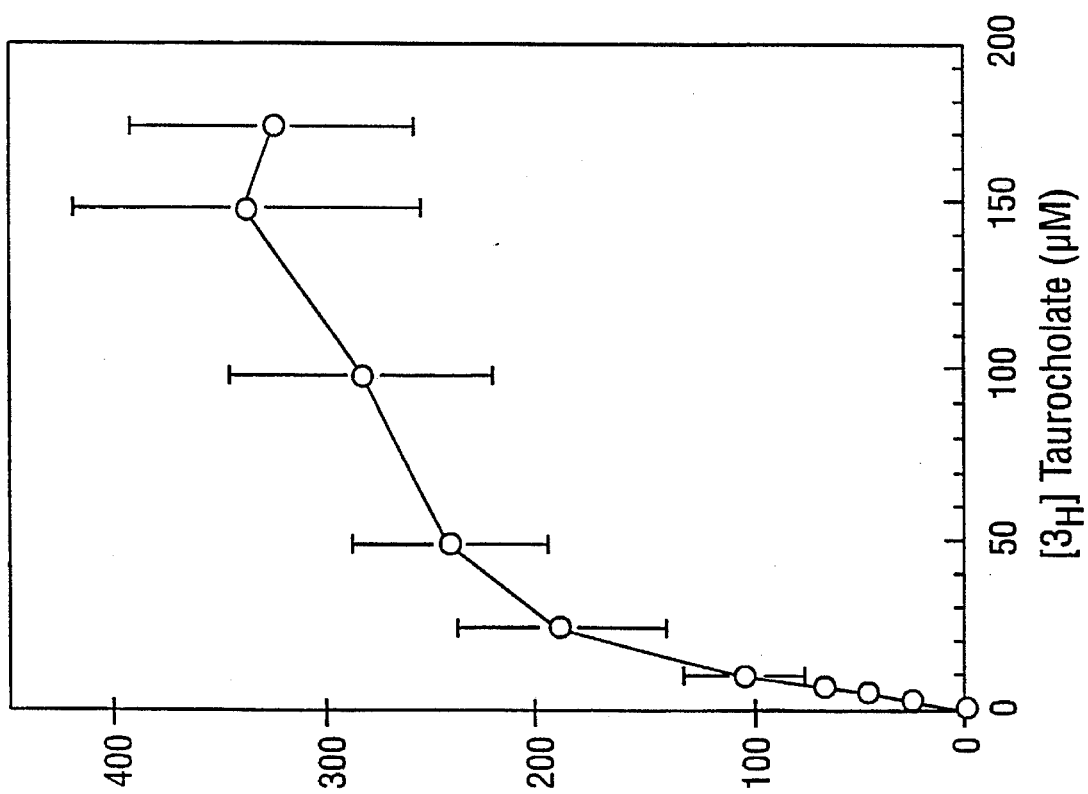
FIG. 5B
FIG. 5A

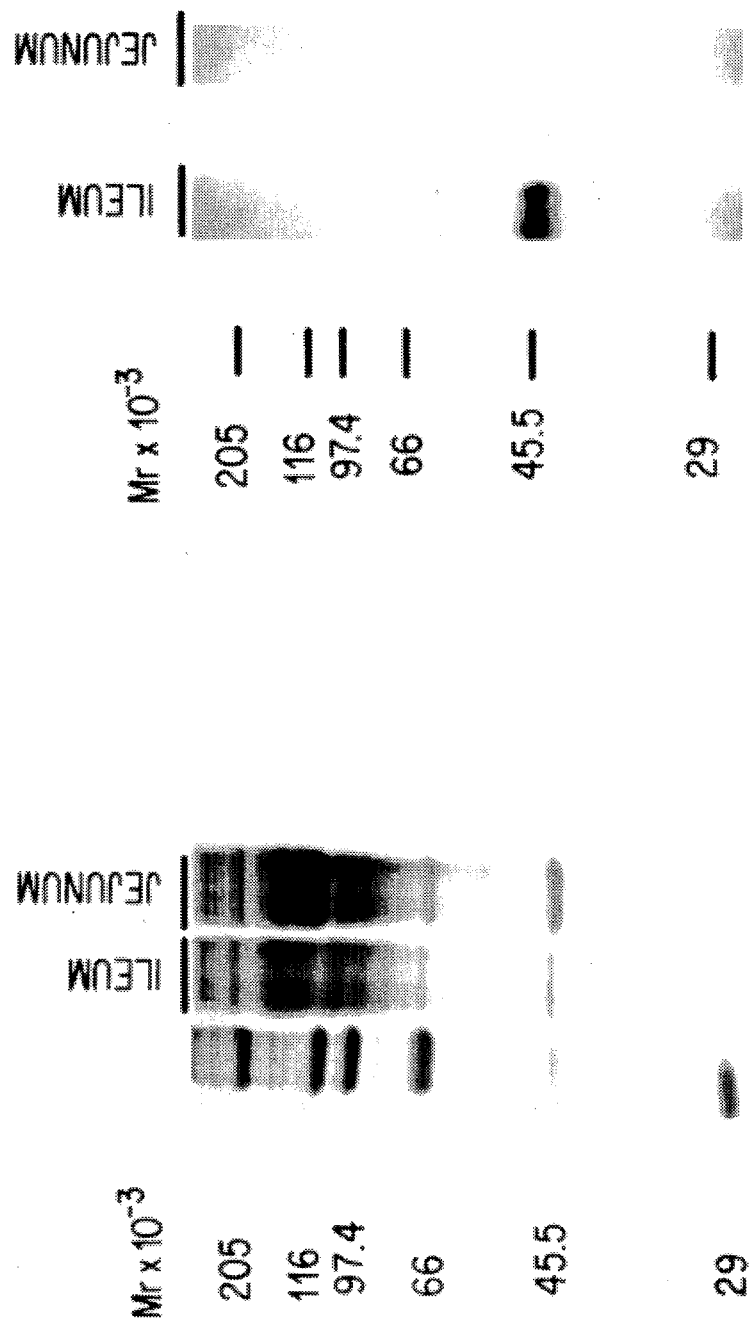

| | | |
|---|---|---|
| HUMAN | MNDPNSCVDNATVCSGASCVVPESNFNNILSVVMSTVLTILLALVMFSMGCNVEIKK | 57 |
| HAMSTER | M DNSSI QN PNAT IC EG DSCI A PESNFN A ILSVVMSTVLTILLALVMFSMGCNVEL HK | |
| HUMAN | FLGHIKRPWGICVGFLCQFGIMPLTGFILSVAFDILPLQAVVVLIIGCCPGGTASNI | 114 |
| HAMSTER | FLGH LR RPWGI M VGFLCQFGIMPLTGF V LSVAFG IL P VQAVVVLI Q GCCPGGTASNI | |
| HUMAN | LAYWVDGDMDLSVSMTTCSTLLALGMMPLCLLIYTKMWVDSGSIVIPYDNIGTSLVA | 171 |
| HAMSTER | LAYWVDGDMDLSVSMTTCSTLLALGMMPLCL E IYTKMWVDSG T IVIPYD S IGTSLVA | |
| HUMAN | LVVPVSIGMFVNHKWPQKAKIILKIGSIAGAILIVLIAVVGGILYQSAWIIAPKLWI | 228 |
| HAMSTER | LV I PVSIGM Y VNHKWPQKAKIILKIGSIAGAILIVLIAVVGGILYQSAW TI E PKLWI | |
| HUMAN | IGTIFPVAGYSLGFLLARIAGLPWYRCRTVAFETGMQNTQLCSTIVQLSFTPEELNV | 285 |
| HAMSTER | IGTI Y P I AGY GL GF E LLARIAG Q PWYRCRTVA L ETG Q QNTQLCSTIVQLSF S PE D LN L | |
| HUMAN | VFTFPLIYSIFQLAFAAIFLGFYVAYKKCHGKNKAEIPESKENGTEPESSFYKANGG | 342 |
| HAMSTER | VFTFPLIYSIF Q I AFAAI L L G A YVAYKKCHGKN N I E LQ E KTD N EM E P R SSFQ ET N KG | |
| HUMAN | FQPDEK | 348 |
| HAMSTER | FQPDEK | |

FIG. 8

ILEAL BILE ACID TRANSPORTER COMPOSITIONS AND METHODS

The government owns rights in the present invention pursuant to grant number DK08718 from the National Institutes of Health.

BACKGROUND OF THE INVENTION

1. Field of the Invention

The present invention relates generally to the fields of sodium/bile acid cotransport systems in the ileum and kidney. Certain embodiments of the invention relate to the medically related fields of the control of blood cholesterol levels and treatments of diabetes, heart disease, liver disease and various digestive disorders. More particularly, the invention concerns the isolation and purification of bile acid cotransporter proteins and cDNA clones encoding the proteins and the use of these proteins and nucleic acids in therapeutic, preventative, genetic counseling and reagent screening applications.

2. Description of the Related Art

Bile acids are acidic sterols synthesized from cholesterol in the liver. Following synthesis, the bile acids are secreted into bile and enter the lumen of the small intestine, where they facilitate absorption of fat-soluble vitamins and cholesterol. Bile acids are then absorbed from the small intestine, returned to the liver via the portal circulation, and resecreted into bile. In the small intestine, bile acids are absorbed by both passive and active mechanisms (Dietschy, 1968). The active absorption of bile acids, first described by Lack and Weiner (1961), has been shown in man and experimental animals to be restricted to the ileum (Krag and Phillips, 1974; Schiff et al., 1972; Lack, 1979).

The first step in the active uptake of bile acids is mediated by a $Na^+$ gradient-driven transporter located at the brush border (apical) membrane of the ileocyte (Wilson, 1981). Once inside the enterocyte, bile acids are transported across the cell to the basolateral membrane and secreted into the portal circulation via a $Na^+$-independent organic anion exchange system (Weinberg et al., 1986). The transport kinetics and specificity of this $Na^+$/bile acid cotransport system have been studied extensively using everted ileal gut sacs (Schiff et al., 1972; Lack, 1979), isolated ileocytes (Wilson et al., 1975; Schwenk et al., 1983), and ileal brush border membranes (Barnard and Ghishan, 1987; Kramer et al., 1992; Wilson and Treanor, 1979).

Although the mechanism of ileal bile acid transport has been characterized, the protein(s) responsible for this process have not been isolated and characterized. In an attempt to identify the proteins involved, photoaffinity studies have been performed using radiolabeled 7,7'-azo-derivatives of taurocholate with ileocytes and ileocyte membrane fractions (Kramer et. al., 1983; Lin et. al., 1990). These studies tentatively identified a brush border (apical) membrane protein of 99 kDa and basolateral membrane proteins of 54 and 59 kDa. More recently, lysylglycocholate-Sepharose affinity chromatography was used to isolate bile acid transporter-enriched ileal brush border membranes for polyclonal antibody production. In immunoblotting experiments, these antibodies detected a number of proteins including a 99 kDa protein in rat ileal brush border and kidney proximal tubule membranes. These antibodies also partially inhibited bile acid transport by isolated ileal brush border membranes (Gong et al., 1991). The tentative identification of a 90-99 kDa protein is also supported by chemical modification studies in rabbit ileum where agents that inhibited bile acid transport into ileal brush border membrane vesicles also blocked photoaffinity labeling of a 90 kDa protein (Kramer et al., 1992).

Notably lacking with the lysylglycocholate-Sepharose affinity chromatography and photoaffinity labeling studies was functional reconstitution of bile acid transport activity. Several candidate bile acid binding proteins previously identified by photoaffinity labeling have since been abandoned, illustrating the difficulties with this technique. For example, candidate 67 kDa and 43 kDa proteins were later shown to be albumin and actin, respectively (Fricker et al., 1982). Also, a candidate 54 kDa protein for the hepatic $Na^+$-independent multispecific anion transporter, has recently been shown to be Protein Disulfide Isomerase (Peter Meier, personal communication). The multispecific transporter has since been identified by expression cloning in Xenopus oocytes and shown to be a 75 kDa protein (Jacquemin et al., 1992). Based on these observations, the 54 kDa protein identified in ileal basolateral membranes by photoaffinity labeling (Lin et al., 1988) may also be Protein Disulfide Isomerase. In addition, a candidate 49 kDa protein for the hepatic $Na^+$-dependent sinusoidal membrane bile acid transporter has been shown to be microsomal epoxide hydrolase (Von Dippe et al., 1993). Whereas the relationship between microsomal epoxide hydrolase and bile acid transport is still unclear, a candidate 40 kDa membrane glycoprotein with bile acid transport properties has independently been identified by expression cloning in Xenopus oocytes (Hagenbuch et al., 1991). Unfortunately, the identity of the ileal bile acid transporter has remained elusive because it has not been purified to homogeneity and functionally reconstituted or identified by cloning and expression.

The enterohepatic circulation of bile acids serves as a continuous link between the liver and small intestine. Disturbances in this cycling of bile acids have dramatic physiological consequences for both organ systems and for cholesterol homeostasis (Hofmann, 1989). This is illustrated by common disturbances of bile acid circulation including cholestasis and intestinal malabsorption. In addition to steatorrhea, bile acid malabsorption also has severe consequences for the colon, where excess bile acid results in watery diarrhea. Whereas the etiology of the bile acid malabsorption is clear in cases of ileal resection or Crohn's disease, specific defects in ileal bile acid transport or its regulation may also be responsible for some cases of chronic idiopathic diarrhea (Read et al., 1980; Heubi et al., 1981).

Bile acid malabsorption or disruption of the bile acid enterohepatic circulation stimulates de novo synthesis of bile acids in the liver. This results in an increased demand for cholesterol by the liver, which is compensated for by enhanced clearance of plasma LDL as well as increased hepatic cholesterol synthesis. If the malabsorption is significant, hepatic bile acid production may be unable to compensate for the loss, resulting in decreased intraluminal bile acid concentrations and a reduced ability to solubilize and absorb biliary and dietary cholesterol. This is the basis for the decreased plasma cholesterol levels and reduced morbidity from cardiovascular disease associated with ileal resection in the POSCH study (Program on the Surgical Control of Hyperlipidemias; Buchwald et al., 1990).

A less radical approach to treatment is the ingestion of polymeric bile acid sequestrants, such as cholestyramine and colestipol. Disruption of the bile acid enterohepatic circulation, especially in combination with HMG CoA reductase inhibitors, increases the number of hepatic LDL receptors and thereby decreases plasma LDL cholesterol levels (Brown and Goldstein, 1986). Despite gaps in the understanding of hepatic synthesis or intestinal conservation of bile acids, this drug regimen is widely used for the treatment of many forms of hypercholesterolemia (Goodman et al., 1988). Based on its remarkable substrate specificity, the ileal $Na^+$-dependent system represents an attractive target for treatment of hypercholesterolemia by interruption of the enterohepatic circulation with specific inhibitors of bile acid transport.

Therefore, bile acid transporter inhibitors are another immediate need in the art, which has not been met because the purified transporter is not available. Previous attempts to design inhibitors relied on the use of intact laboratory animals, isolated small intestine or kidney tissue, or isolated intestinal enterocytes. The use of laboratory animals instead of tissue culture cells or purified bile acid transporter enzyme made large scale drug screens prohibitively cumbersome and expensive. The number of compounds which could be assayed was also limited with small intestinal sections or isolated enterocytes, which are difficult to prepare and viable for only a period of hours.

Obviously, one would like to use the human ileal and renal bile acid transporters in these drug screens in the event that the animal model does not accurately mimic the human condition. However, human tissue is not readily available and very few human intestinal or kidney cell lines which express bile acid transporter activity exist. Currently, a human colon cancer cell line ($CaCo_2$) has been discovered which expresses very small amounts of bile acid transporter activity. Unfortunately, this cell line requires special culture conditions and would be difficult to adapt to a high throughput assay format.

Therefore, there exists a need for a purified bile acid transporter to be used in the diagnosis and treatment of numerous human and animal conditions which are affected by this important system. In addition, a purified transporter would have utility in the screening of natural and man made products with possible pharmaceutical properties in the treatment of cholesterol related diseases and digestive and hepatic disorders.

SUMMARY OF THE INVENTION

The present invention seeks to overcome these and other drawbacks inherent in the prior art by providing the first definitive identification and isolation of mammalian ileal bile acid transporters. With the use of the present invention, high levels of bile acid transporter activity can be expressed in transfected tissue culture cells or in prokaryotic cells. In addition, cell lines which permanently express high levels of the transporter can be readily generated and used, for example in a high throughput assay to rapidly screen for inhibitors of the bile acid transporter.

In certain embodiments the present invention is a segment of DNA and particularly a segment of DNA which encodes an ileal/renal bile acid cotransporter polypeptide comprising an amino acid sequence in accordance with the amino acid sequence as set forth herein as seq id no: 2 and seq id no: 4. This DNA segment also comprises the nucleic acid sequence as sort forth herein as seq id no: 1 and seq id no: 3. It is understood that in addition to the DNA sequence coding strand, the reverse complement of the coding sequence, the RNA sequence encoded by the DNA segment and the reverse complement of the RNA sequence are also encompassed by the present claimed invention.

As used herein the term "reverse complement" is used to define the strand of nucleic acid which will hybridize to the first nucleic acid sequence to form a double stranded molecule under stringent conditions. Stringent conditions are those that allow hybridization between two nucleic acid sequences with some degree of homology, but precludes hybridization of random sequences. For example, hybridization at low temperature and/or high ionic strength is termed low stringency and hybridization at high temperature and/or low ionic strength is termed high stringency. The temperature and ionic strength of a desired stringency are understood to be applicable to particular probe lengths, to the length and base content of the sequences and to the presence of formamide in the hybridization mixture.

It is understood in the art that a nucleic acid sequence will hybridize with a complementary nucleic acid sequence under high stringency conditions even though some mismatches may be present. Such closely matched, but not perfectly complementary sequences are also encompassed by the present invention. For example, differences may occur through genetic code degenerency, or by naturally occurring or man made mutations and such mismatched sequences would still be encompassed by the present claimed invention.

It is also understood that the DNA segment of the present invention may be under the control of a promoter. The promoter may be the normal promoter which controls the expression of the DNA segment in its native tissue, or it may be a recombinant promoter. By recombinant promoter is meant a promoter derived from another source, either another within the same cell or from a different type of cell or even from a different organism. The promoter sequence is then joined to the DNA segment in an upstream position (5') from the start of the gene. Preferred promoters are cytomegalovirus major immediate early gene promoter, simian virus 40 late gene promoter and Baculovirus *Autographa californica* nuclear polyhedrosis virus polyhedrin gene promoter. Alternatively, the promoter may be an inducible promoter such as the lactose operon promoter.

The DNA segment of the present invention may also comprise a vector capable of replicating within a cell. In particular, the DNA segment may comprise a recombinant vector. A large number of vectors are available commercially and are well known to those in the art. In general, a vector is compatible with a particular cell type such as prokaryotic, eukaryotic, yeast, plant, insect, etc. The matching of compatible vectors and host cells is well known and routinely practiced in the art. Preferred vectors in the practice of the present invention are pCMX and pCMV5.

As used herein, the term "engineered" or "recombinant" cell is intended to refer to a cell into which a recombinant gene, such as a gene encoding a bile acid cotransporter has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene (i.e., they will not contain introns), a copy of a genomic gene, or will include genes positioned adjacent to a promoter not naturally associated with the particular introduced gene. Preferred cell lines to be used in the present invention are CHO cells, MDCK, $CaCo_2$ and BHK cells, and more preferred are COS-1A cells.

In certain embodiments, the vector which comprises the DNA segment of the present invention will be an expression vector. In this embodiment, the DNA segment encoding the ileal/renal bile acid cotransporter will be transcribed into mRNA and the mRNA will be translated into a polypeptide.

Thus, the recombinant cell will express the ileal/renal bile acid cotransporter polypeptide. The vector in this embodiment will comprise the signal sequences to express the gene in the particular cell type. For instance the promoter/enhancer regions, translational start sites and downstream signals such as the polyadenylation site if necessary, will be compatible with the host cell transcription/translational mechanisms.

It is understood that smaller nucleic acid segments which comprise as their nucleic acid sequence the nucleic acid sequence of seq id no: 1 or seq id no: 3 are also encompassed by the present invention. For example, nucleic acid segments comprising at least a ten, fifteen, twenty, thirty, fifty, one hundred, or one thousand, or even up to a 4,000 nucleotide long stretch which corresponds to the nucleic acid sequence of seq id no: 1 or seq id no: 3 and including the nucleic acid sequence of seq id no: 1 or seq id no: 3 are also a part of and are included in the present claimed invention.

In certain embodiments of the present invention, the recombinant host cell which comprises a vector and expresses the ileal/renal bile acid cotransporter, may be further defined as comprising a nucleic acid fragment of up to 10,000, up to 5,000 or up to 3,000 basepairs in length. It may further be defined as comprising a nucleic acid fragment of up to 1,000, up to 500, up to 100 or even up to 50 basepairs in length. The vector may be an RNA molecule or more preferably a DNA molecule.

In certain alternate embodiments, the present invention is a polypeptide, a protein, or even a peptide, comprising as a part of its amino acid sequence the amino acid sequence as set forth in seq id no: 2 or seq id no: 4, or even a polypeptide or protein with the amino acid sequence of seq id no: 2 or seq id no: 4. It is also understood that amino acid fragments or peptides of the present invention will have utility, for example as antigenic epitopes, in the production of antibodies or as screening agents. Therefore, a peptide which comprises as a part of its amino acid sequence at least a four amino acid stretch, at least a ten amino acid stretch, at least a twenty amino acid stretch, at least a fifty amino acid stretch, at least a one hundred amino acid stretch, or even up to a three hundred forty eight amino acid stretch corresponding to the amino acid sequence of seq id no: 2 or seq id no: 4 will be encompassed by the scope and the spirit of the appended claims.

An important use of the peptide fragments of the present invention is the production of antibodies which are immunoreactive with said peptides. These antibodies will have wide utility as diagnostic agents for the various disorders discussed in the present disclosure as well as use as possible inhibitors of bile acid transport. Therefore antibodies which are produced with the peptides or polypeptides of the present invention, or those antibodies which are found to be immunoreactive with the peptides or polypeptides of the present invention are also a part of this invention. The antibodies may be polyclonal antibodies or monoclonal antibodies and may be derived from any source such as goat, mouse, bovine, equine, simian or any other source, even including recombinantly produced antibodies. The production of anti-idiotype antibodies is also well known in the art, and any such anti-idiotypic antibodies are also encompassed by the present invention.

An important embodiment of the present invention is a method of screening substances as effectors of ileal/renal bile acid cotransport. The discovery of the nucleic acid and amino acid sequences of the present invention provides a new and valuable method of screening naturally occurring and man made substances for their ability to inhibit or even to stimulate ileal and/or renal bile acid cotransport. By the use of the present invention, and particularly by the use of recombinant cells which express the ileal/renal bile acid cotransporter, a high throughput assay is possible for the first time.

This screening assay comprises obtaining a candidate substance which can come from any source. For example, it is proposed that compounds isolated from natural sources such as fungal extracts, plant extracts, bacterial extracts, higher eukaryotic cell extracts, or even extracts from animal sources, or marine, forest or soil samples, may be assayed for the presence of potentially useful pharmaceutical agents. In addition, man made substances which would include, but are not limited to, synthetic bile acid derivatives, peptides or other compounds designed de novo based on the predicted protein structure of the ileal/renal bile acid cotransporter, can also be screened for possible use as pharmaceutical agents. It is also understood that antibodies and other isolated or purified, but naturally occurring compounds could be screened by this process.

In the screening process, the recombinant cells would be deposited on a surface such as the wells of a microtiter plate or in any suitable medium or container. A substrate to indicate cotransport would also be present in contact with the cells. A preferred substrate is $^3$H-taurocholate, but other substances or taurocholate labelled by other means are also possible and would fall within the scope of the present invention. Some distinguishable groups of cells would then be exposed to the candidate substance and some would not be so exposed. A measurement of the taurocholate uptake, for example would then be compared between cells which were or were not incubated with the candidate substance. An increase in uptake over the control would indicate an activating substance and a decrease in uptake over the control would indicate an inhibitor. It is understood that the inhibition could occur at any level of the expression of bile acid cotransport, including gene transcription, RNA processing, mRNA translation, post translational modification and even protein transport or at any other level that would have the overall effect of activation or inhibition of bile acid transport. Preferred cells to be used in the assay would be Chinese hamster ovary cells (CHO) for example, however, any cells which express the ileal/renal bile acid cotransporter would be acceptable and would be encompassed by the present claimed invention. Examples of other cell types include MDCK, CaCo$_2$, BHK, COS AND 293 cells.

Alternatively, candidate substances could be screened with the use of reporter genes under the control of bile acid transporter promoters. In this embodiment, the reporter gene would be expressed in the presence and absence of a candidate substance as in the previously described screening assays. A change in level of the reporter gene product in the presence of the candidate substance relative to the level in the absence of the candidate substance would indicate an effector of bile acid transporter expression. Preferred reporter genes include, but are not limited to the β-galactosidase gene from *E. coli* and chloramphenicol acetyltransferase.

ABBREVIATIONS

The following abbreviations are used throughout the present disclosure:

IBAT, ileal Na$^+$/bile acid cotransporter; LBAT, liver Na$^+$/ bile acid cotransporter; GAPD: glyceraldehyde-3- phosphate dehydrogenase; TEA: tetraethylammonium; BSP, bromosulfophthalein; DIDS, 4,4'-diisothiocyano-2,2'-disulfonic acid stilbene; TC: taurocholate; GC: glycocholate; TCDC: taurochenodeoxycholate; TDC: taurodeoxycholate; SDS: sodium dodecyl sulfate.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 3. Blot hybridization of mRNA from hamster tissues. Poly(A)$^+$ RNA (5 μg) from the indicated tissues was subjected to electrophoresis on a 1.2% agarose gel containing 2.2M formaldehyde and blotted onto a GeneScreen membrane (Dupont-NEN). Upper panel, hybridization was carried out in 50% formamide buffer at 42° C. for 11 hours with a mixture of three single-stranded uniformly $^{32}$P-labeled IBAT cDNA probes (4.2×10$^6$ cpm/ml). The filter was washed in 0.2×SSC containing 0.1% (w/v) SDS at 65° C. for 30 minutes and exposed to Amersham Hyperfilm with an intensifying screen for 12 hours at −70° C. The migration of RNA standards run in an adjacent lane are indicated. Lower panel, the filter was stripped and rehybridized with a uniformly $^{32}$P-labeled human glyceraldehyde-3-phosphate dehydrogenase probe (GAPD; 1×10$^{17}$ cpm/ml), washed, and exposed to Amersham Hyperfilm for 1 hour at −70° C.

FIG. 5A. Kinetics of taurocholate uptake in pIBAT-transfected COS cells. COS cells were plated and transfected as described in the description of FIG. 4 (immediately above). On day 4, the cells were incubated in medium B supplemented with the indicated concentration of [$^3$H] taurocholate (45 mCi/mmol). After 15 minutes at 37° C., the medium was removed, and each cell monolayer washed and processed to determine cell-associated protein and radioactivity. Each value represents the mean ± standard deviation (n=4).

FIG. 5B. Eadie-Hofstee analysis of taurocholate uptake in pIBAT-transfected COS cells. The uptake data from FIG. 5A was analyzed and revealed a $K_m$ for taurocholate uptake of 33 μM and a $V_{max}$ of 396 pmol min$^{-1}$ mg$^{-1}$ protein.

FIG. 7. An antibody was made to a synthetic peptide corresponding to amino acids 335–348 (SEQ ID NO: 5) of the hamster ileal Na$^+$/bile acid cotransporter as described in Example V. To demonstrate the specificity of the antibody, 100 μg of rat jejunal or ileal brush border membrane protein was denatured and reduced in Laemmli sample buffer containing 2% (w/v) SDS and 2.5% (v/v) β-mercaptoethanol. The protein was then subjected to electrophoresis on a 10% SDS-polyacrylamide gel and either stained with coomassie blue ("Coomassie") or transferred to a nitrocellulose filter ("Immunoblot").

FIG. 8. The deduced amino acid sequences of the human IBAT (HIBAT, seq id no: 4) and hamster IBAT (seq id no: 2) were compared and sequence differences are boxed. Overall, the hamster and human ileal bile acid transporter sequences exhibit 84% identity and 90% similarity.

DETAILED DESCRIPTION OF THE PREFERRED EMBODIMENTS

Figure 1A:
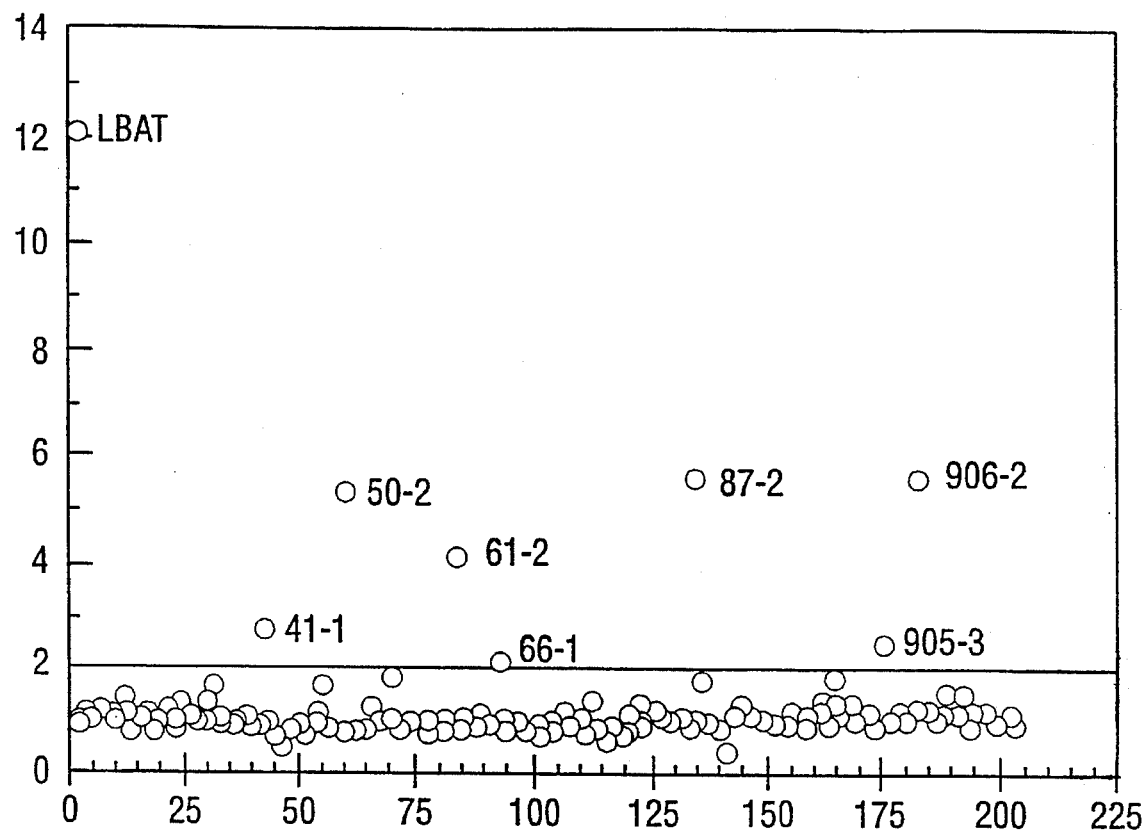
FIG. 1A. Expression cloning of ileal Na$^+$/bile acid cotransporter. For each transfection experiment, 10 to 24 pools of cDNA plasmids were transiently transfected into duplicate dishes of COS cells. The horizontal axis denotes cDNA plasmid pools of approximately 3000 clones each. The activity is expressed as [$^3$H] taurocholate uptake relative to pCMV-βgal transfected COS cells. [$^3$H] taurocholate uptake into pCMV-βgal transfected cells was 1.56±0.52 pmoles hour$^{-1}$ mg$^{-1}$ protein (n=17).

Active uptake of bile acids from the lumen of the small intestine is mediated by an ileal Na$^+$-dependent bile acid transport (IBAT) system. To identify components of this transport system, an expression cloning strategy was employed to isolate a hamster ileal cDNA that exhibits bile acid transport activity. By Northern blot analysis, mRNA for the cloned transporter was readily detected in ileum and kidney but absent from liver and proximal small intestine.

It was found that the transporter cDNA encoded a 348 amino acid protein with seven potential transmembrane domains and three possible N-linked glycosylation sites. The amino acid sequence was 35% identical and 63% similar to the rat liver Na$^+$/bile acid cotransporter (LBAT, Hagenbuch et al., 1991). IBAT exhibited little sequence identity with the Na$^+$/glucose cotransporter or other members of the large family of 12 transmembrane domain Na$^+$ cotransport proteins (Wright et al., 1992).

Hydropathy analysis of the sequences from the LBAT and IBAT transporters predicted a similar topology with seven transmembrane domains, an extracellular amino terminus, and a cytosolic carboxyl terminus. Both LBAT and IBAT were also found to lack the predicted Na$^+$ binding motif which had been identified in a number of 12 transmembrane domain Na$^+$ cotransport proteins (Deguchi et al., 1990; Wright et al., 1992). Overall, the predicted topology for IBAT showed greater similarity to the seven transmembrane domain proteins, such as rhodopsin and G protein coupled receptors (Khorana, 1992; Baldwin, 1993).

The amino acid homology between the liver and ileal Na$^+$/bile acid cotransport proteins is clustered in both the predicted transmembrane domains and the cytoplasmic and exoplasmic loops. For example, a repeated motif is found in the second and third predicted transmembrane domains of both proteins. A block of sequence identity also exists in the putative extracellular loop that lies between the sixth and seventh transmembrane domains. The hamster IBAT cDNA encodes three potential N-linked glycosylation sites. Interestingly, the two N-linked glycosylation sites adjacent to the initiator methionine are conserved between the liver and ileal bile acid transporters. Preliminary studies by the inventor using an in vitro translation/translocation system (Blobel and Dobberstein, 1975) indicate that IBAT is modified by N-linked glycosylation. The utilization of particular glycosylation sites as well as the contribution of the conserved amino acid domains to transporter function are yet to be determined.

In agreement with the properties described for ileal bile acid transport (Wilson, 1981), the isolated IBAT clone exhibited uptake activity that was Na$^+$-dependent, saturable, and bile acid-specific. Using an everted gut sac model (Lack, 1979), ileal bile acid uptake has been studied extensively and found to specifically require Na$^+$ ions. A similar Na$^+$ requirement was also demonstrated for IBAT, where taurocholate uptake was stimulated over 100-fold in the presence of Na$^+$ but not other cations (see FIG. 4).

In addition, taurocholate uptake by the expressed IBAT was saturable and exhibited an apparent Km of 33 µM. This Km was similar to the values of 36, 37, and 65 µM reported for taurocholate uptake by rabbit ileal brush border membranes, human ileal brush border membranes, and CaCo$_2$ cells, respectively (Kramer et al., 1992; Barnard and Grishan, 1987; Chandler et al., 1993). Like these in vitro measurements, the apparent Km for taurocholate transport in pIBAT-transfected COS cells was considerably less than the apparent Km of 5–10 mM determined for taurocholate uptake using in situ ileal preparations (Lewis and Root, 1990; Marcus et al., 1991). One possible explanation for these differences may be the presence of a diffusion barrier such as the mucous layer that is present in the intact intestine but absent in isolated cells and membranes (Wilson and Dietschy, 1974).

In the studies of transport specificity, dihydroxy bile acids such as taurochenodeoxycholic acid and taurodeoxycholic acid were more effective competitors of [$^3$H] taurocholate uptake by IBAT-transfected COS cells than the trihydroxy bile acid, taurocholate. These results were similar to those obtained using everted ileal gut sacs and in situ perfusions (Lack, 1979; Schiff et al., 1972). In addition, as reported for rabbit ileal brush border membrane vesicles (Kramer et al., 1992), taurocholate uptake by IBAT was not inhibited by the cholephilic organic compound, bromosulfophthalein (BSP) or the bifunctional anion transport inhibitor 4,4'-diisothiocyano-2,2'-disulfonic acid stilbene (DIDS).

By Northern blot analysis, IBAT mRNA was found in intestinal regions and tissues known to express Na$^+$/bile acid cotransport activity. Under stringent conditions, the IBAT cDNA hybridized to mRNA from hamster kidney as well as ileum, suggesting that IBAT may also be responsible for the Na$^+$/bile acid cotransport activity present in the renal tubules (Weiner et al., 1964; Wilson et al., 1981).

In the intestine, IBAT mRNA expression was restricted to the ileum and distal jejunum. These results are consistent with a large number of studies using perfused intestine, perfused intestinal sections, everted gut sacs, isolated enterocytes, and isolated enterocyte brush border membranes which identified the distal ileum as the major site of $Na^+$ dependent bile acid uptake in the intestine (Hofmann, 1977; Wilson, 1981). These results are also consistent with Xenopus oocyte expression studies, where mRNA for $Na^+$/bile acid cotransporter activity was detected in ileum but not duodenum or jejunum from rabbit and guinea pig (Sorscher et al., 1992). Interestingly however, Xenopus oocyte injection experiments using pig intestine mRNA detected $Na^+$/bile acid cotransporter mRNA in proximal as well as distal intestine (Mullins et al., 1992). While the basis for this species difference in the intestinal gradient of bile acid transporter expression is unknown, the availability of an ileal $Na^+$/bile acid cotransporter cDNA should facilitate the study of its expression down the cephalocaudal axis of the intestine in different species.

The $Na^+$-dependence, saturability, and bile acid specificity of transport, as well as the tissue specificity of mRNA, indicates that the IBAT cDNA described herein does express the $Na^+$/bile acid cotransporter activity previously described in ileum (Hofmann, 1977, Wilson, 1981). The isolated transporter cDNA clone encodes a protein of 348 amino acids with an approximate molecular mass of 38 kDa, and three potential N-linked glycosylation sites. This molecular mass clearly differs from the 90 and 99 kDa proteins previously identified by affinity labeling using photolabile derivatives of taurocholate (Lin et al., 1990; Kramer et al., 1992). The relationship between IBAT and the photoaffinity labeled proteins is unclear. The 90 to 99 kDa protein may represent a posttranslationally modified form of the 38 kDa $Na^+$/bile acid cotransporter or possibly a dimer which is poorly dissociated by SDS polyacrylamide gel electrophoresis. For example, the seven transmembrane domain protein, rhodopsin, is known to form dimers and oligomers that are refractory to dissociation under the denaturing and reducing conditions used for SDS polyacrylamide gel electrophoresis (DeGrip, 1982; Fliesler and Basinger, 1985). Alternatively, it is possible that ileal enterocytes harbor more than one brush border membrane $Na^+$/bile acid cotransporter.

With the availability of a cDNA encoding an active ileal $Na^+$/bile acid cotransporter, it is now possible to express large amounts of the cotransporter in cultured cells. This ability will allow the molecular mechanism of ileal bile acid transport to be elucidated. This information will be crucial for the design of inhibitors and possibly useful mutations of the cotransporter. Further, it is now possible to examine the relationship between the protein encoded by this cDNA and proteins which have been identified by other means and which may be involved in bile acid transport.

Expression of Bile Acid Transporter Activity

The present technology utilizes ileal enterocytes isolated from laboratory animals. These preparations express high levels of transport activity (>1000 pmoles of taurocholate transported per minute per mg of cell protein) but are viable for very short periods of time (1–6 hours). The bile acid transporter-transfected tissue culture cells of the present invention express similar levels of bile acid transport activity (600 to 1000 pmoles of taurocholate transported per minute per mg of cell protein), and can be passaged in culture for months.

Present technology also utilizes a human colon carcinoma-derived cell line, $CaCo_2$ cells. While these cells can be passaged for weeks, $CaCo_2$ cells require specialized culture conditions to express their ileal cell and bile acid transporter properties. In addition, $CaCo_2$ cells only weakly express bile acid transport activity (approximately 10 pmoles of taurocholate transported per minute per mg of cell protein). This activity is 60 to 100-fold less than the activity of bile acid transporter-transfected tissue culture cells of the present invention. Recent improvements in $CaCo_2$ cell culture conditions have substantially increased their bile acid transport activity (Chandler et al., 1993). However, the culture conditions required are cumbersome and the high levels of activity are limited to certain clonal lines within a narrow window of cell passages. The present invention overcomes these restrictions.

The isolation of the cDNA segment of the present invention will allow the expression of large quantities of the ileal/renal bile acid transporter protein in various expression vectors and host cells. Examples of appropriate expression systems include, but are not limited to bacterial expression of recombinant plasmids and/or phage, recombinant baculovirus-infected insect cells and mammalian tissue culture cells such as Chinese hamster ovary (CHO) cells. The ileal/renal bile acid transporter cDNA may also be used for stable expression of the ileal/renal bile acid transporter protein in transgenic animals such as mice.

Since the isolated cDNAs encompass the entire coding sequence, one may proceed to prepare an expression system for the preparation of recombinant ileal/renal bile acid cotransporter. The engineering of DNA segment(s) for expression in a prokaryotic or a eukaryotic system may be performed by techniques generally known to those of skill in recombinant expression. It is believed that virtually any expression system may be employed in the expression of the ileal/renal bile acid cotransporter.

Prokaryotic hosts may be preferred for expression of the ileal/renal bile acid cotransporter for some applications. Some examples of prokaryotic hosts are various *E. coli* strains, bacilli such as *Bacillus subtilis*, or other enterobacteriaceae such as *Salmonella typhimurium* or *Serratia marcescens*, and various Pseudomonas species may be used, with *E. coli* being the most preferred.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, a well known plasmid useful for transforming *E. coli* is pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins.

In addition, phage vectors containing replicon and control sequences that are compatible with the host microorganism can be used as transforming vectors in connection with these hosts. For example, the phage lambda pGEM™-11 may be utilized in making a recombinant phage vector which can be used to transform host cells, such as *E. coli* LE392. The most preferred prokaryotic vectors include pKK233-2, which utilizes the strong IPTG-inducible $P_{trc}$ promoter and the pT7 series which utilize the T7 RNA polymerase promoter system.

Some promoters commonly used in recombinant DNA construction include the B-lactamase (penicillinase) and lactose promoter systems, as well as viral promoters. While these are the most commonly used, other microbial promoters have been discovered and utilized, and details concerning their nucleotide sequences are readily available, enabling a skilled worker to ligate them functionally into plasmid vectors.

In addition to prokaryotes, eukaryotic microbes, such as yeast cultures may also be used. *Saccharomyces cerevisiae*, or common baker's yeast is a commonly used eukaryotic microorganism, although a number of other strains are available. For expression in Saccharomyces, the plasmid YRp7, for example, may be used. This plasmid contains the trpl gene which provides a selection marker for a mutant strain of yeast lacking the ability to grow in tryptophan. The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase or other glycolytic enzymes such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the expressed sequence to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, the aforementioned glyceraldehyde-3-phosphate dehydrogenase, and enzymes responsible for maltose and galactose utilization. Any plasmid vector containing a yeast-compatible promoter, an origin of replication, and termination sequences is suitable.

Of particular interest is the use of insect cells as a host for baculoviral expression vectors. Currently, the preferred baculovirus expression systems utilize the lyric insect virus known as *Autographa californica* multiply enveloped nuclear polyhedrosis virus. For production of recombinants in insect cells using recombinant baculoviral vectors, it is desirable to utilize the polyhedron gene's powerful promoter and control sequences. This can be accomplished by replacing the baculoviral polyhedron gene with the cDNA to be expressed. Baculoviral expression vectors ordinarily include all the original baculoviral genes except the polyhedron gene and may include additional marker genes such as the β-galactosidase gene. Examples of such useful baculoviral preparations include Linearized AcMNPV Baculovirus DNA, Linearized AcRP23.lacZ Baculovirus DNA, and Linearized AcUW1.lacZ Baculovirus DNA. After cloning the cDNA to be expressed in a suitable transfer plasmid, the cDNA can be transferred in place of the baculovirus polyhedron gene by the process of recombination. The transfer plasmids contain baculoviral DNA sequences to promote the recombination with linear baculoviral DNA and may also contain additional marker genes such as the β-galactosidase gene. Suitable transfer plasmids include pBlueBac III, pBlueBacHis, and pAcUW21. The recombination to assemble the recombinant baculovirus which expresses the cDNA of interest and production of the protein product from that cDNA is performed in insect cells or insect hosts. Examples of suitable host cells include *Spondoptera frugiperda* Sf9 cells, Sf21 cells, and MG1 cells.

In addition to microorganisms and insects, cultures of cells derived from vertebrate organisms may also be used as hosts. In principle, any such vertebrate or invertebrate cell culture is workable. However, vertebrate cells are a preferred host, and propagation of vertebrate cells in culture (tissue culture) has become a routine procedure in recent years. Examples of such useful host cell lines are VERO and HeLa cells, Chinese hamster ovary (CHO) cell lines, and W138, BHK, COS-7, 293 and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, cytomegalovirus, Adenovirus 2, and most frequently Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the Hind III site toward the BglI site located in the viral origin of replication. Further, it is also possible, and often desirable, to utilize promoter or control sequences normally associated with the desired gene sequence, provided such control sequences are compatible with the host cell systems.

The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

It is understood in the art that to bring a coding sequence under the control of a promoter, one positions the 5' end of the transcription initiation site of the transcriptional reading frame of the protein between about 1 and about 50 nucleotides "downstream" of (i.e., 3' of) the chosen promoter. In addition, where eukaryotic expression is contemplated, one will also typically desire to incorporate into the transcriptional unit which includes the cotransporter protein, an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

It is contemplated that the ileal/renal bile acid cotransporter of the invention may be "overexpressed", i.e., expressed in increased levels relative to its natural expression in ileal or renal cells, or even relative to the expression of other proteins in the recombinant host cell. Such overexpression may be assessed by a variety of methods, including radio-labelling and/or protein purification. However, simple and direct methods are preferred, for example, those involving SDS/PAGE and protein staining or Western blotting, followed by quantitative analyses, such as densitometric scanning of the resultant gel or blot. A specific increase in the level of the recombinant protein or peptide in comparison to the level in natural ileal or renal cells is indicative of overexpression, as is a relative abundance of the specific protein in relation to the other proteins produced by the host cell as determined, e.g., by visibility on a gel.

Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the inventor does not exclude the possibility of employing a genomic version of a particular gene where desired.

Amino Acid Segments

An important embodiment of the amino acid sequences of the present invention is the use of the ileal/renal bile acid transporter amino acid sequence to model the protein structure for use in inhibitor design, for example. Initially, this entails a comparison of the protein sequence disclosed herein with the sequences of related proteins. In this way, the transmembrane domains and the putative glycosylation sites have been determined. Also, by comparing the amino acid sequence of the present disclosure with proteins of similar function (bile acid binding, cotransport, etc.) sequences may be identified which are directly involved in those functions. In particular, amino acid residues which are conserved over a range of species are good candidates for involvement in functional active sites or binding sites. The amino acid sequence of the bile acid transporter will thus be useful for designing superior inhibitors. For example, potential inhibiting substances can be tested for binding to amino acid segments known to be involved in various functions of the cotransporter, and would thus be screened for potential inhibition of activity.

An alternate use of the ileal/renal bile acid transporter protein sequence will be to model the protein structure for use in designing compounds as vehicles for drug targeting. For example, bile acid analogues have been recently used as targeting agents to direct drug delivery specifically to the liver or ileum. Drugs such as HMG CoA reductase inhibitors were coupled to a bile acid analog and shown to be specifically and efficiently taken up by the liver. Analogous systems can be designed for use with the ileal/renal transporter, and the sequences of the present invention will be useful for designing these new drug delivery vehicles.

Production of Antibodies

Another important embodiment of the amino acid sequences of the ileal bile acid transporter is their use in the production of antibodies. This amino acid sequence has been used to synthesize a peptide as antigen for monospecific antibody development. For example, the peptide, Ser-Phe-Gln-Glu-Thr-Asn-Lys-Gly-Phe-Gln-Pro-Asp-Glu-Lys, (Seq id no: 5), which corresponds to amino acids 335–348 of the hamster ileal/renal bile acid transporter has been used successfully as antigen for monospecific antibody development. The cDNA clone has also been used to express portions of the ileal bile acid transporter in bacteria as antigen for monospecific antibody development.

Antibodies, both polyclonal and monoclonal, specific for the bile acid cotransporter of the present invention may be prepared using conventional immunization techniques, as will be generally known to those of skill in the art. A composition containing antigenic epitopes of the bile acid cotransporter can be used to immunize one or more experimental animals which will then proceed to produce specific antibodies against the bile acid cotransporter protein. Typically an animal used for production of antisera is a rabbit, a mouse, a rat, a hamster or a guinea pig. Because of the relatively large blood volume of rabbits, a rabbit is a preferred choice for production of polyclonal antibodies. Polyclonal antisera may be obtained, after allowing time for antibody generation, simply by bleeding the animal and preparing serum samples from the whole blood.

As is well known in the art, a given polypeptide may vary in its immunogenicity. It is often necessary therefore to couple the immunogen (e.g., a polypeptide of the present invention) with a carrier. Exemplary and preferred carriers are keyhole limpet hemocyanin (KLH), Purified Peptide Derivative of Tuberculin (PPD) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As is also well known in the art, immunogenicity to a particular immunogen can be enhanced by the use of non-specific stimulators of the immune response known as adjuvants. Exemplary and preferred adjuvants include complete Freund's adjuvant, incomplete Freund's adjuvants and aluminum hydroxide adjuvant.

The amount of immunogen used in the production of polyclonal antibodies depends inter alia, upon the nature of the immunogen as well as the animal used for immunization. A variety of routes can be used to administer the immunogen (subcutaneous, intramuscular, intradermal, intravenous and intraperitoneal). The production of polyclonal antibodies is monitored by sampling blood of the immunized animal at various points following immunization. When a desired level of immunogenicity is obtained, the immunized animal can be bled and the serum isolated and stored.

A monoclonal antibody of the present invention can be readily prepared through use of well-known techniques such as those exemplified in U.S. Pat. No 4,196,265, incorporated herein by reference. Typically, a technique involves first immunizing a suitable animal with a selected antigen (e.g., a polypeptide of the present invention) in a manner sufficient to provide an immune response. Rodents such as mice and rats are preferred animals. Spleen cells from the immunized animal are then fused with cells of an immortal myeloma cell. Where the immunized animal is a mouse, a preferred myeloma cell is a murine NS-1 myeloma cell, and a more preferred cell line is the NS1/1 Ag 4.1 myeloma cell.

The fused spleen/myeloma cells are cultured in a selective medium to select fused spleen/myeloma cells from the parental cells. Fused cells are separated from the mixture of non-fused parental cells, for example, by the addition of agents that block the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides. Where azaserine is used, the media is supplemented with hypoxanthine.

This culturing provides a population of hybridomas from which specific hybridomas are selected. Typically, selection of hybridomas is performed by culturing the cells by single-clone dilution in microtiter plates, followed by testing the individual clonal supernatants for reactivity with an antigen-polypeptide. The selected clones can then be propagated indefinitely to provide the monoclonal antibody.

By way of specific example, to produce an antibody of the present invention, mice are injected intraperitoneally with about 1–200 μg of an antigen comprising a polypeptide of the present invention. B lymphocyte cells are stimulated to grow by injecting the antigen in association with an adjuvant such as complete Freund's adjuvant (a non-specific stimulator of the immune response containing killed *Mycobacterium tuberculosis*). At some time (e.g., at least two weeks) after the first injection, mice are boosted by injection with a second dose of the antigen mixed with incomplete Freund's adjuvant.

A few weeks after the second injection, mice are tail bled and the sera titered by immunoprecipitation against radiolabeled antigen. Preferably, the process of boosting and titering is repeated until a suitable titer is achieved. The spleen of the mouse with the highest titer is removed and the spleen lymphocytes are obtained by homogenizing the spleen with a syringe. Typically, a spleen from an immunized mouse contains approximately $5 \times 10^7$ to $2 \times 10^8$ lymphocytes.

Mutant lymphocyte cells known as myeloma cells are obtained from laboratory animals in which such cells have been induced to grow by a variety of well-known methods. Myeloma cells lack the salvage pathway of nucleotide biosynthesis. Because myeloma cells are tumor cells, they can be propagated indefinitely in tissue culture, and are thus denominated immortal. Numerous cultured cell lines of myeloma cells from mice and rats, such as murine NS-1 myeloma cells, have been established. Myeloma cells are combined under conditions appropriate to foster fusion with the normal antibody-producing cells from the spleen of the mouse or rat injected with the antigen/polypeptide of the present invention. Fusion conditions include, for example, the presence of polyethylene glycol. The resulting fused cells are hybridoma cells. Like myeloma cells, hybridoma cells grow indefinitely in culture.

Hybridoma cells are separated from unfused myeloma cells by culturing in selection medium such as HAT media (hypoxanthine, aminopterin, thymidine). Unfused myeloma cells lack the enzymes necessary to synthesize nucleotides from the salvage pathway and are killed in the presence of aminopterin, methotrexate, or azaserine. Unfused lymphocytes also do not continue to grow in tissue culture. Thus, only cells that have successfully fused (hybridoma cells) can grow in the selection media.

Each of the surviving hybridoma cells produces a single antibody. These cells are then screened for the production of the specific antibody immunoreactive with an antigen/polypeptide of the present invention. Single cell hybridomas are isolated by limiting dilutions of the hybridomas. The hybridomas are serially diluted many times and, after the dilutions are allowed to grow, the supernatant is tested for the presence of the monoclonal antibody. The clones producing that antibody are then cultured in large amounts to produce an antibody of the present invention in convenient quantity.

By use of a monoclonal antibody of the present invention, specific polypeptides of the invention can be recognized as antigens, and thus identified. Once identified, those polypeptides can be isolated and purified by techniques such as antibody-affinity chromatography. In antibody-affinity chromatography, a monoclonal antibody is bound to a solid substrate and exposed to a solution containing the desired polypeptide. The polypeptide-antigen is removed from the solution through an immunospecific reaction with the bound antibody. The polypeptide is then easily removed from the substrate and purified.

It is proposed that the monoclonal antibodies of the present invention will find useful application in standard immunochemical procedures, such as ELISA and Western blot methods, as well as other procedures which may utilize antibody specific to bile acid transporter epitopes. Additionally, it is proposed that monoclonal antibodies specific to the particular bile acid transporter may be utilized in other useful applications. For example, their use in immunoabsorbent protocols may be useful in purifying native or recombinant bile acid transporters from various species or variants thereof. A particularly useful application of such antibodies is in purifying native or recombinant bile acid transporters, for example, using an antibody affinity column. Such antibodies would also be useful as immunohistochemical or immunoblotting reagents in the diagnosis of chronic idiopathic diarrhea associated with bile acid malabsorption, ileal disease and bile acid related kidney disease. The operation of all such immunological techniques will be known to those of skill in the art in light of the present disclosure.

Renal Bile Acid Cotransporter

Using the materials and methods of the present invention, the major bile acid transporter present in the kidney is shown to be identical to the ileal bile acid transporter. Based on these studies, the same complementary DNA clone can be used to develop inhibitors of the renal bile acid reabsorption, to identify renal bile acid cotransporters from other species, and other utilities analogous to those described herein for the ileal transporter. Therefore, all such uses of the renal bile acid transporter are included within the scope and spirit of the present claimed invention.

Nucleic Acid Hybridization

The DNA sequences disclosed herein will find utility as probes or primers in nucleic acid hybridization embodiments. As such, it is contemplated that oligonucleotide fragments corresponding to the sequences of seq id no: 1 for stretches of between about 17 nucleotides to about 30 nucleotides will find particular utility, with even longer sequences, e.g., 40, 50, 100, even up to full length, being more preferred for certain embodiments. The ability of such nucleic acid probes to specifically hybridize to bile acid cotransporter-encoding sequences will enable them to be of use in a variety of embodiments. For example, the probes can be used in a variety of assays for detecting the presence of complementary sequences in a given sample. However, other uses are envisioned, including the use of the sequence information for the preparation of mutant species primers, or primers for use in preparing other genetic constructions.

Nucleic acid molecules having stretches of 10, 20, 30, 50, or even of 100 nucleotides or so, complementary to seq id no: 1 or seq id no: 3 will also have utility as hybridization probes. These probes will be useful in a variety of hybridization embodiments, such as Southern and Northern blotting in connection with analyzing transporter structural or regulatory genes in diverse tissues and in various species. The total size of the fragment, as well as the size of the complementary stretches, will ultimately depend on the intended use or application of the particular nucleic acid segment. Smaller fragments will generally find use in hybridization embodiments, wherein the length of the complementary region may be varied, such as between about 17 and about 100 nucleotides, or even up to 2263 according to the complementary sequences one wishes to detect.

The use of a hybridization probe of about 17 nucleotides in length allows the formation of a duplex molecule that is both stable and selective. Molecules having complementary sequences over stretches greater than 17 bases in length are generally preferred, though, in order to increase stability and selectivity of the hybrid, and thereby improve the quality and degree of specific hybrid molecules obtained. One will generally prefer to design nucleic acid molecules having gene-complementary stretches of about 20 nucleotides, or even longer where desired. Such fragments may be readily prepared by, for example, directly synthesizing the fragment by chemical means, by application of nucleic acid reproduction technology, such as the PCR technology of U.S. Pat. No. 4,603,102 (incorporated herein by reference) or by introducing selected sequences into recombinant vectors for recombinant production.

Accordingly, the nucleotide sequences of the invention may be used for their ability to selectively form duplex molecules with complementary stretches of bile acid transporter genes or cDNAs. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and or high temperature conditions, such as provided by 0.02M–0.15M NaCl at temperatures of 50° C. to 70° C. Such selective conditions tolerate little, if any, mismatch between the probe and the template or target strand, and would be particularly suitable for isolating the hamster ileal and renal bile acid cotransporter genes.

Preferred hybridization conditions and temperatures include a solution containing 50% (volume/volume) formamide, 5× Denhardt's solution, 6×SSC, 0.1% (weight/volume) SDS, and 100 µg/ml salmon sperm DNA, and 1 mM sodium pyrophosphate at 37° C. For nucleotide sequences longer than 50 nucleotides, preferred wash conditions include a solution containing 2×SSC/0.5% SDS at 25° C. for 30 min followed by one or more washes in a solution containing 0.2×SSC/0.5% SDS at 60° C. for 30 min per wash. For nucleotide sequences shorter than 50 nucleotides, preferred wash conditions include a solution containing 2×SSC/1% SDS at 25° C for 30 min followed by one or more washes in a solution containing 2×SSC/1% SDS at 50° C. for 30 min.

Of course, for some applications, for example, where one desires to prepare mutants employing a mutant primer strand hybridized to an underlying template or where one seeks to isolate bile acid cotransporter-encoding sequences from related species, functional equivalents, or the like, less stringent hybridization conditions will typically be needed in order to allow formation of the heteroduplex. In these circumstances, one may desire to employ conditions such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmentally undesirable reagents. In the case of enzyme tags, colorimetric indicator substrates are known which can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase.

In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the circumstances based on the particular criteria required (depending, for example, on the G+C contents, type of target nucleic acid, source of nucleic acid, size of hybridization probe, etc.). Following washing of the hybridized surface to remove nonspecifically bound probe molecules, specific hybridization is detected, or even quantified, by means of the label.

Longer DNA segments will often find particular utility in the recombinant production of peptides or proteins. DNA segments which encode peptide antigens from about 15 to about 50 amino acids in length, or more preferably, from about 15 to about 30 amino acids in length are contemplated to be particularly useful, as are DNA segments encoding entire bile acid transporter proteins. DNA segments encoding peptides will generally have a minimum coding length on the order of about 45 to about 150, or to about 90 nucleotides. DNA segments encoding full length proteins may have a minimum coding length on the order of about 1,044 nucleotides for a protein in accordance with seq id no: 2 or seq id no: 4.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is contemplated that a nucleic acid fragment of almost any length may be employed, with the total length preferably being limited by the ease of preparation and use in the intended recombinant DNA protocol. For example, nucleic acid fragments may be prepared in accordance with the present invention which are up to 10,000 base pairs in length, with segments of 5,000 or 3,000 being preferred and segments of about 1,000 base pairs in length being particularly preferred.

It will be understood that this invention is not limited to the particular nucleic acid and amino acid sequences of seq id nos: 1–5. Therefore, DNA segments prepared in accordance with the present invention may also encode biologically functional equivalent proteins or peptides which have variant amino acids sequences. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged.

DNA segments encoding a bile acid transporter gene may be introduced into recombinant host cells and employed for expressing a bile acid transporter protein. Alternatively, through the application of genetic engineering techniques, subportions or derivatives of selected transporter genes may be employed. Equally, through the application of site-directed mutagenesis techniques, one may re-engineer DNA segments of the present invention to alter the coding sequence, e.g., to introduce improvements to the antigenicity of the protein or to test for binding site mutants in order to examine transport activity at the molecular level. Where desired, one may also prepare fusion peptides, e.g., where the transporter coding regions are aligned within the same expression unit with other proteins or peptides having desired functions, such as for immunodetection purposes.

An important use of the nucleic acid segments will be in the study of ileal disease. The nucleic acid segments of the present invention may be adapted for use in for example, in situ hybridization, RNA blotting, and DNA blotting for diagnostic purposes in ileal disease. In particular, diseases related to mutations in the ileal and renal bile acid cotransporters will be detectable by the use of the nucleic acid segments of the present invention.

This application of the nucleic acid segments of the present invention will also be useful in genetic screening and counseling. Congenital defects in the ileal/renal bile acid transporter are rare, but life-threatening if not recognized early. The cloned ileal/renal bile acid transporter can be used to identify a variety of genetically-linked DNA sequence variations (polymorphisms) for the ileal/renal bile acid transporter gene. In cases where a family history of bile acid malabsorption is suspected, the nucleic acid segments of the present invention can be used for prenatal or neonatal diagnosis.

In a further embodiment, the nucleic acid sequences of the present invention may be used to synthesize anti-sense or ribozyme probes to down-regulate expression of the bile acid transporter in the ileum for use as plasma cholesterol-lowering agents. For example, an anti-sense probe that is designed to hybridize to the mRNA synthesized from the bile acid cotransporter gene would, when introduced into the ileal cells, disrupt translation of the mRNA and would hence lower the expression of the cotransporter. The lowered levels of cotransporter would function to lower plasma cholesterol levels. A similar embodiment would be possible in the kidney cells for use as plasma bile acid-lowering agents in the treatment of cholestasis, jaundice, liver cirrhosis, primary biliary cirrhosis, and sclerosing cholangitis.

Screening Assays

In still further embodiments, the present invention concerns a method for identifying new bile acid transport inhibitory compounds, which may be termed as "candidate substances." It is contemplated that this screening technique will prove useful in the general identification of any compound that will serve the purpose of inhibiting ileal and/or renal bile acid transport. It is further contemplated that useful compounds in this regard will in no way be limited to bile acid analogues. In fact, it may prove to be the case that the most useful pharmacological compounds for identification through application of the screening assay will serve to inactivate the transport through a tight binding or other chemical interaction.

Accordingly, in screening assays to identify pharmaceutical agents which affect bile acid transport, it is proposed that compounds isolated from natural sources such as synthetic bile acid derivatives, fungal extracts, plant extracts, bacterial extracts, higher eukaryotic cell extracts, or even extracts from animal sources, or marine, forest or soil samples, may be assayed for the presence of potentially useful pharmaceutical agents. It will be understood that the pharmaceutical agents to be screened could also be derived from chemical compositions or man-made compounds other than synthetic bile acid derivatives. In important aspects, the candidate substances may be anti-bile acid transporter antibodies, including polyclonal and monoclonal antibodies. The suspected agents could also include proteins and peptides, such as those derived from recombinant DNA technology or by other means, including peptide synthesis. The active compounds may include fragments or parts of naturally-occurring compounds or may be only found as active combinations of known compounds which are otherwise inactive.

To identify a candidate substance capable of inhibiting bile acid transport, one would first obtain a recombinant cell line capable of expressing ileal/renal bile acid transport. Naturally, one would measure or determine the activity of the bile acid transport in the absence of the added candidate substance. One would then add the candidate substance to the cell growth media or expose the cells in an appropriate way to the candidate substance and re-determine the ability of the cells to transport bile acid in the presence of the candidate substance. A candidate substance which reduces the activity of the bile acid transporter relative to the activity in its absence is indicative of a candidate substance with inhibitory capability. The indicator in the screening assays will preferably be taurocholate and more preferably tritium labeled taurocholate. For an example of a taurocholate uptake assay, see Example III, infra.

In the most preferred embodiment, stably transfected ileal/renal bile acid transporter over-expressing cell lines will be used for high throughput assays to screen synthetic bile acid derivatives, fungal extracts, plant extracts, bacterial extracts, higher eukaryotic cell extracts or others as mentioned above, for potential inhibitors of the bile acid transporter for use as plasma cholesterol-lowering agents. In addition, these various extracts will be screened for use in the treatment of disorders such as cholestasis, jaundice, primary biliary cirrhosis, sclerosing cholangitis and others.

Promoter/Reporter Gene Fusions

The present invention also provides candidate substance screening methods which are based upon whole cell assays and which, preferably, employ a reporter gene that confers on its recombinant hosts a readily detectable phenotype to indicate expression from the cotransporter gene promoter. Generally, reporter genes encode a polypeptide not otherwise produced by the host cell which is detectable by analysis of the cell culture, e.g., by fluorometric, radioisotopic or spectrophotometric analysis of the cell culture. Exemplary enzymes include esterases, phosphatases, proteases (tissue plasminogen activator or urokinase) and other enzymes capable of being detected by their activity, as will be known to those skilled in the art. A preferred example is *E. coli* beta-galactosidase, which produces a color change upon cleavage of an indigogenic substrate. Another preferred example is the enzyme chloramphenicol acetyltransferase (CAT) in which activity is preferably determined by detection of a radioactively labelled substrate by scintillation counting or by thin layer chromatography followed by autoradiography. A more preferred example is the enzyme luciferase in which activity is preferably determined by detection of light using a luminometer.

Another class of reporter genes which confer detectable characteristics on a host cell are those which encode polypeptides, generally enzymes, which render their transformants resistant against toxins, e.g., the neo gene which protects host cells against toxic levels of the antibiotic G418; or a gene encoding dihydrofolate reductase, which confers resistance to methotrexate. Genes of this class are not generally preferred since the phenotype (resistance) does not provide a convenient or rapid quantitative output. Resistance to antibiotic or toxin requires days of culture to confirm, or complex assay procedures if other than a biological determination is to be made.

Other genes for use in the screening assay herein are those capable of transforming hosts to express unique cell surface antigens, e.g., viral env proteins such as HIV gp120 or herpes gD, which are readily detectable by immunoassays. However, antigenic reporters are not preferred because, unlike enzymes, they are not catalytic and thus do not amplify their signals.

The polypeptide products of the reporter gene are secreted, intracellular or, as noted above, membrane bound polypeptides. If the polypeptide is not ordinarily secreted it is fused to a heterologous signal sequence for processing and secretion. In other circumstances the signal is modified in order to remove sequences that interdict secretion. Preferably, however, the products of the reporter gene are lodged in the intracellular or membrane compartments. Then they can be fixed to the culture container, e.g., microtiter wells, in which they are grown, followed by addition of a detectable signal generating substance such as a chromogenic substrate for reporter enzymes.

In general, the sequences of the present invention are employed to control transcription and expression of the reporter gene. The process which in its entirety leads to enhanced transcriptional promotion is termed "activation." Alternatively, the process which in its entirety leads to reduced transcriptional promotion is termed "inhibition." The mechanism by which a successful candidate substance acts is not material since the objective is to promote or repress gene expression, and particularly, to activate or inhibit the ileal/renal bile acid transporter gene, by whatever means will function to do so.

The promoter, whether a hybrid or the native bile acid cotransporter promoter, is ligated to DNA encoding the reporter gene by conventional methods. The bile acid cotransporter promoter is obtained by in vitro synthesis or recovered from genomic DNA. It is ligated upstream of the start codon of the reporter gene. The promoter also will contain an AT-rich region (TATA box), located between the bile acid cotransporter promoter and the reporter gene start codon. The region 3' to the coding sequence for the reporter gene will contain a transcription termination and polyadenylation site, for example the hepatitis B polyA site. The promoter and reporter gene are inserted into a replicable vector and transfected into a cloning host such as $E.$ $coli$. The host is then cultured and the replicated vector is recovered in order to prepare sufficient quantities of the construction for later transfection into a suitable eukaryotic host.

The host cells used in the screening assay herein generally are mammalian cells, and are preferably cell lines which may be used in connection with stable and/or transient transfection assays. It is also important for inhibitor screening, that the cell line be one in which the gene is constitutively expressed so that inhibition can be measured. Cell lines should be relatively easy to grow in large scale culture. Also, they should contain as little native background as possible considering the nature of the reporter polypeptide. Examples include the Hep G2, VERO, HeLa, CHO, W138, BHK, COS-7, and MDCK cell lines, with CHO cells being preferred. Since the ileal/renal bile acid transporter is selectively expressed in the ileum and kidney, cells of intestinal and renal origin are more preferred. Examples include $CaCo_2$ cells and OK cells. The vector is cotransfected into the desired host, stable transformants selected and, optionally, the reporter gene and its controlling promoter are amplified in order to increase the screening assay sensitivity. This is accomplished in conventional fashion by cotransforming the host with the reporter gene and a selectable marker gene such as DHFR (for DHFR minus host cells such as CHO) or DHFR and neo for other hosts, followed by the application of a selection agent.

The screening assay typically is conducted by growing the transformants to confluency in microtiter wells, adding 5 to 50 µM [$^3$H] taurocholate with 0.1 to 100-fold serial molar proportions of candidate therapeutic agents to a series of wells. The signal level is determined after an incubation period that is sufficient to demonstrate expression in controls incubated solely with 5 to 50 µM [$^3$H] taurocholate. The wells containing varying proportions of candidate are then evaluated for signal activation. Candidates that demonstrate dose related enhancement/repression of reporter gene transcription or expression are then selected for further evaluation as clinical therapeutic agents.

Candidate substances that are found to inhibit the expression of the ileal bile acid transporter gene expression in the ileum will be useful as plasma cholesterol-lowering agents and those that inhibit the renal bile acid transporter gene expression in the kidney will be useful for the treatment of cholestasis, jaundice, primary biliary cirrhosis, and sclerosing cholangitis. Candidate substances that are found to activate the expression of the ileal bile acid transporter gene expression in the ileum will have use in patients with ileal disease or Crohn's disease and in patients who have undergone ileal resection.

It should be understood that the screening method herein is useful notwithstanding that effective candidates may not be found, since it would be a practical utility to know that bile acid cotransporter activators and/or inhibitors do not exist. The invention consists of providing a method for screening for such candidates, not in finding them.

Gene Therapy

The ileal/renal bile acid transporter cDNA will also be useful for gene therapy to restore bile acid uptake activity to patients whose ileum has been surgically resected for diseases like Crohn's disease, patients who were born with congenital defects in the bile acid transporter, and patients who suffer from adult-onset chronic idiopathic bile acid diarrhea.

The characterization of the ileal $Na^+$-dependent bile acid cotransporter will have utility in a wide range of clinical applications as disclosed above. In addition to the clinical applications, understanding the mechanism and regulation of intestinal and renal bile acid transport will yield new and useful information directly related to the role of bile acids in lipid absorption, cholesterol homeostasis, and the pathogenesis and treatment of hypercholesterolemia and gastroenterological disease.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

CLONING OF THE ILEAL BILE ACID TRANSPORTER

Materials and Methods

Certain standard molecular biology techniques were employed in the present study (Sambrook et al., 1989). Total cellular RNA was isolated by the guanidinium thiocyanate/

CsCl centrifugation procedure (Chirgwin et al., 1979). Poly(A)+ RNA was isolated using oligo(dT)-cellulose spin columns from Pharmacia LKB Biotechnology Inc. For Northern blot analysis, poly(A)+ RNA was fractionated on 1.2% agarose gels containing 2.2 M formaldehyde, transferred to GeneScreen (Dupont-NEN) and hybridized with single-stranded $^{32}$P-labeled M13 DNA probes (Church & Gilbert, 1984). Restriction fragments derived from the IBAT cDNA were inserted into M13 and pBluescript KS II (Stratagene) vectors and sequenced on both strands by the dideoxy chain termination method using the M13 universal sequencing primer or pBluescript-specific primers (Sambrook et al., 1989).

Construction of pCMV-Liver Bile Acid Transporter Plasmid

The polymerase chain reaction (Saiki et al., 1988) was used to obtain a rat liver Na+/bile acid cotransporter (LBAT) cDNA. This clone was used as a positive control to optimize the bile acid transporter expression screening strategy. To obtain a liver bile acid transporter clone, first strand cDNA was synthesized from rat liver poly(A)+ RNA. For the PCR, oligonucleotide primers corresponding to nucleotides 113–133 and 1193–1216, which flanked the amino- and carboxyl-terminal sequences of the rat LBAT, were used (Hagenbuch et al., 1991). Following amplification, a product of the appropriate size (1104 base pairs) was excised from a 0.8% (w/v) agarose gel, and isolated by electroelution. The PCR product was treated with T4 DNA polymerase, phosphorylated with T4 polynucleotide kinase, and ligated into Sma I-cut pCMV$^2$ (Anderson et al., 1989). The authenticity of the bile acid transporter insert was verified by dideoxy sequencing.

Construction of cDNA Expression Library

Male golden Syrian hamsters (90–150 g) were purchased from Sasco (Omaha, Nebr.) and maintained on a normal chow diet (ground Wayne Lab Blox 8604; Allied Mills, Chicago, Ill.) and a 12-h light/12-h dark cycle for at least 10 days prior to use.

Hamster ileal poly(A)+ RNA was used to construct a size-selected cDNA library with a kit purchased from Invitrogen (catalog number L0804-15). Poly(A)+ RNA (5 µg) was denatured with methylmercury hydroxide at room temperature prior to first strand synthesis. Double-stranded oligo(dT)-primed cDNA was synthesized and ligated to Bst XI adapters according to the manufacturer's protocol. cDNAs greater than 2200 base pairs in length were excised from a 0.8% (w/v) agarose gel, isolated by electroelution, and then ligated into the Bst XI sites of the plasmid expression vector pCMX (Davis et al., 1991). The library was titered by electroporation into *E. coli* HB101 cells and contained approximately $1.2 \times 10^7$ independent recombinants. Aliquots of the library were electroporated into *E. coli* HB101 cells, spread onto LB plates containing 50 µg/ml ampicillin, and grown for 12 hours at 37° C. Pools of colonies (approximately $3 \times 10^3$ independent cDNAs per pool) were scraped from the plates, grown for 4 hours in 25-ml cultures of SOC medium with ampicillin, and plasmid DNA was purified using Qiagen-tip 20 columns (Qiagen Inc., Chatsworth, Calif.).

Expression Cloning of Ileal Bile Acid Transporter

Pools of cDNA clones were transfected into COS cells, and subsequently analyzed for uptake of [$^3$H] taurocholate in a transient assay. On day 0, dishes of $5 \times 10^5$ cells per 60-mm dish were plated in medium A. On day 1, duplicate dishes of cells were each transfected with 2 µg of the library plasmid pool by the DEAE-dextran method (Esser et al., 1988). On day 4, the cells were incubated with medium B supplemented with 5 µM [$^3$H] taurocholate (2.0–2.6 Ci/mmol). After incubation for 1 hour at 37° C., the medium was removed, and each cell monolayer was washed 5 times with ice-cold PBS plus 0.2% (w/v) BSA and 1 mM taurocholate, then once with ice-cold PBS alone. The cell monolayer was then dissolved in 0.1 N NaOH and aliquots were taken to determine cell-associated protein and radioactivity. Seven library plasmid pools that expressed [$^3$H] taurocholate uptake activity were identified, and one pool was progressively subdivided into smaller pools (sib selection) until a single positive clone was obtained.

Two control assays were routinely performed for each transfection study. As a negative control, COS cells were transfected with 2 µg of pCMV-βgalactosidase (pCMV-βgal; Briggs et al., 1993). As a positive control, COS cells were transfected with 2 ng of pCMV-LBAT plus 2 µg of pCMV-βgal.

Results

Starting with the size-fractionated hamster ileal cDNA expression library, plasmid DNA was prepared from cultures of 1000–5000 independent bacterial transformants and introduced into COS-1 cells using a DEAE-dextran transfection procedure. The transfected cells were then assayed for [$^3$H] taurocholate uptake activity. COS-1 cells were selected for the expression assays since preliminary studies indicated that mock or pCMV-gal transfected COS cells lack a Na+-dependent taurocholate uptake activity. A total of 202 pools representing approximately 650,000 clones were screened yielding 7 pools which exhibited bile acid uptake activity two to six-fold greater than the pCMV-βgal transfected COS cells. FIG. 1A summarizes the hamster ileal library screening.

Figure 1B:
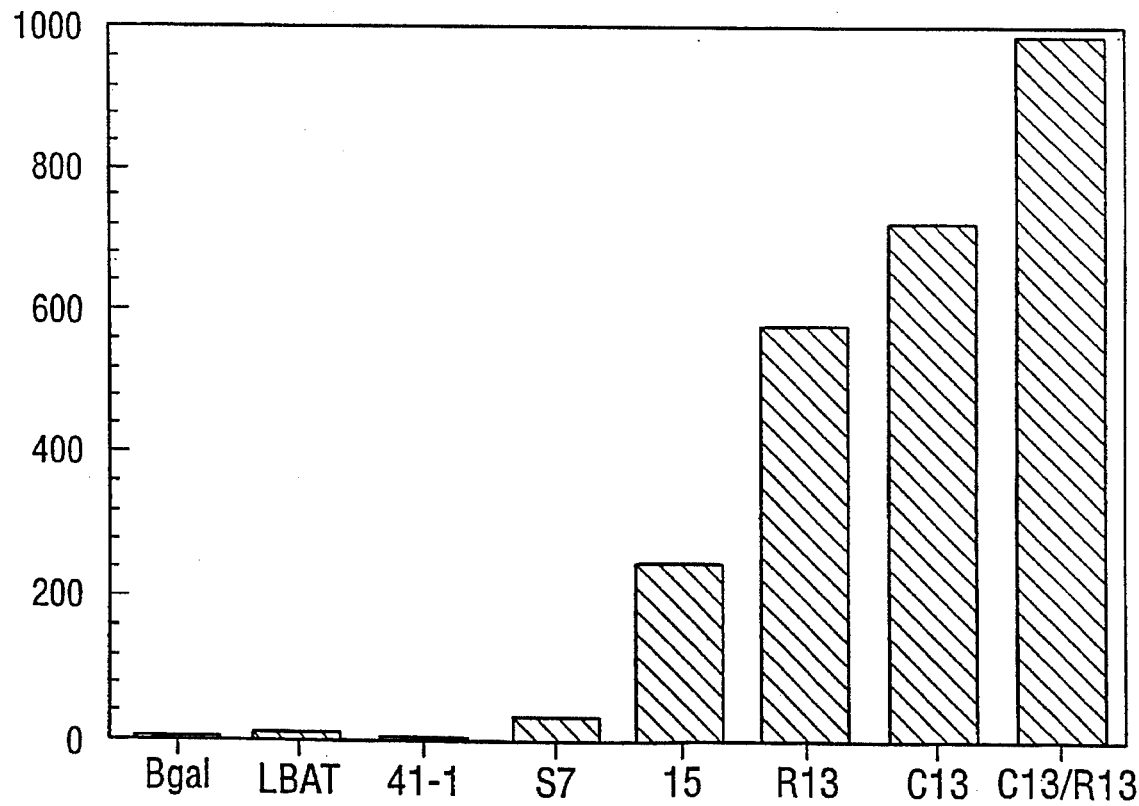
FIG. 1B. Purification of the pIBAT cDNA clone. Positive pool 41-1 was subdivided into 18 pools, of which the data for subfraction 7 (S7) is shown. Positive pool 41-1/S7 was subdivided into 48 pools, of which the data for subfraction 15 is shown. Two hundred colonies from subpool 41-1/S7/15 were randomly picked and plated onto two 10×10 matricies. Pools of cDNA plasmids were prepared from bacterial cultures of each row (1–20) and each column (1–20) and assayed for [$^3$H] taurocholate uptake. Four positive pools were identified, and the data is shown for column 13, row 13, as well as the single clone at the intersection of column 13 and row 13 (C13/R13). [$^3$H] taurocholate uptake into control DNA transfected cells was 0.98±0.29 pmoles hour$^1$ mg$^1$ protein (n=10). As a positive control, [$^3$H] taurocholate uptake for COS cells transfected with 2 ng of pCMV-LBAT plus 2 μg of pCMV-βgal is shown.

From positive pool 41-1, 18 pools of approximately 500 clones each were prepared and one subpool (41–1/S7) was found to be positive in the taurocholate uptake assay. This pool was further subfractionated into 48 pools of approximately 50 clones each, and 6 of these subpools exhibited significant taurocholate uptake activity. Two hundred individual clones from plasmid subpool 41-1/S7/S15 were then plated onto two 10×10 matricies and plasmid pools corresponding to each row and column were prepared. Two rows and two columns were found to exhibit significant taurocholate uptake activity. The four clones at the intersection of the positive rows and columns were then assayed individually, and two of the clones were determined to be positive. The two positive clones were identical by restriction digest analysis and one clone (C13/R13) was designated pIBAT (ileal Na+/bile acid cotransporter) and used for further study. Transfection of the C13/R13 cDNA clone into COS cells stimulated [$^3$H] taurocholate uptake almost 1000-fold (FIG. 1B).

Using the polymerase chain reaction with pIBAT-specific oligonucleotides, the 6 remaining pools from the original expression cloning screen were examined and determined to contain IBAT cDNA clones. To isolate the additional clones, pIBAT was used to screen the 6 positive pools by colony hybridization. Mapping and partial sequencing of the 4 longest clones revealed different lengths for the 5'- and 3'-untranslated regions, but no apparent differences in the predicted coding sequence.

EXAMPLE II

SEQUENCE ANALYSIS OF THE ILEAL BILE ACID TRANSPORTER

Methods

Sequences were analyzed using programs obtained from the Genetics Computer Group Sequence Analysis Software Package, Version 7.1 (Devereux et al., 1984).

Results

The IBAT DNA sequence was determined and the corresponding amino acid sequence deduced. The hamster IBAT cDNA encodes a protein of 348 amino acids (seq id no: 2) with a calculated molecular mass of 37,894 Da. The predicted initiator methionine lies within an appropriate consensus for initiation of translation (Kozak, 1987) and is preceded by a 5'-untranslated region of 108 nucleotides which contains an in-frame stop codon. The translation termination codon is followed by a 3'-untranslated region of 1108 nucleotides which did not extend to the poly(A) tail.

Figure 2:
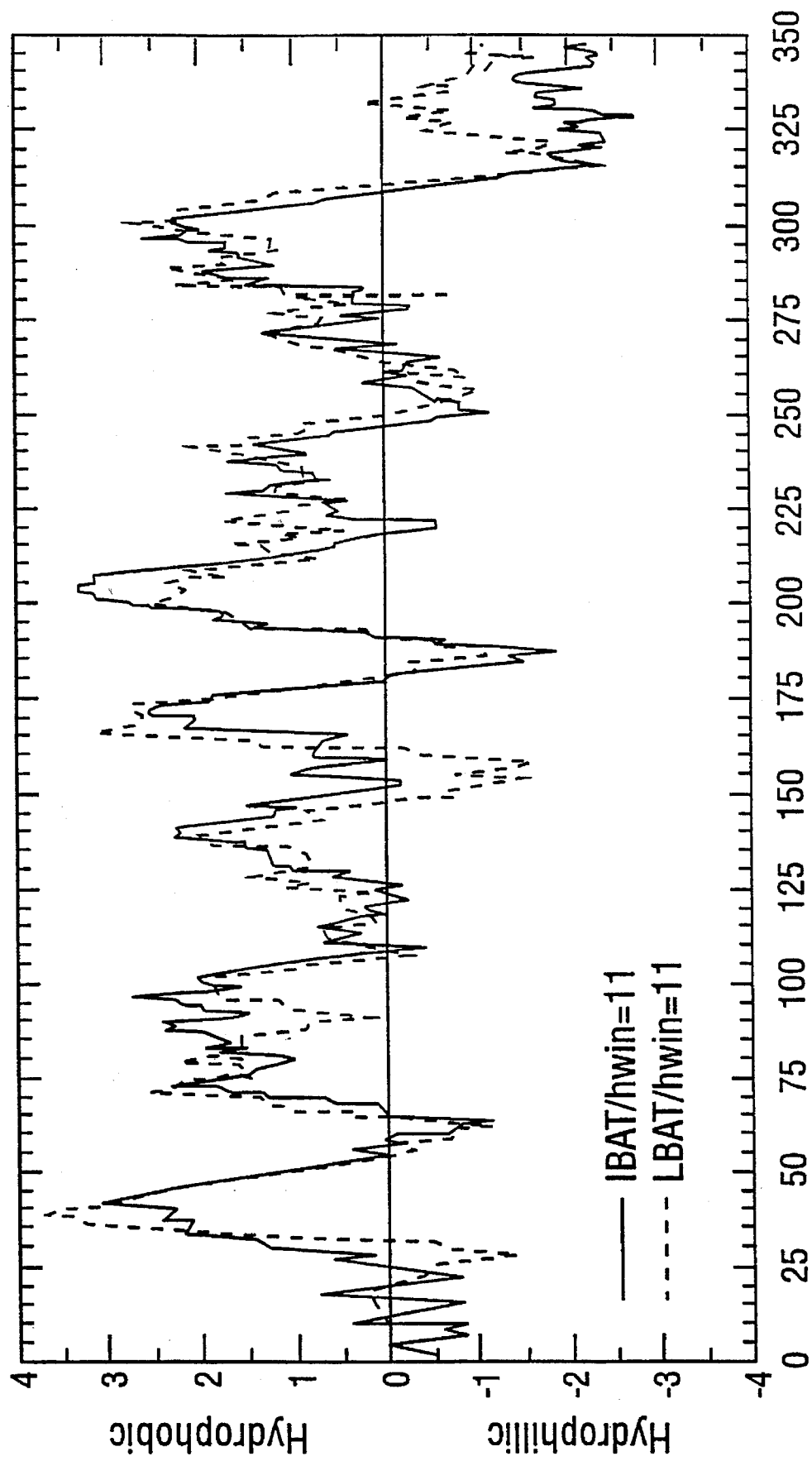
FIG. 2. Hydropathy plot of amino acid sequences of the hamster ileal and rat liver Na$^+$/bile acid cotransporters. Increasing numerical values correspond to increased hydrophobicity. The residue specific hydropathy index was calculated over a window of 11 residues by the method of Kyte and Doolittle (1982) using the Genetics Computer Group Sequence Analysis Software Package, Version 7.1 (Devereux et al., 1984). The plot shows an alignment of amino acids 1–348 of IBAT and amino acids 1–343 of LBAT. For maximal alignment, a gap of 5 amino acids was inserted at the amino terminus of the LBAT sequence. The X axis refers to the amino acid residue number in the IBAT sequence.

A search of available protein and nucleic acid databases revealed that the hamster IBAT protein sequence was 35% identical and 63% similar to the rat LBAT (Hagenbuch et al., 1991). In addition, the two proteins share similar hydropathy profiles, suggesting that both proteins assume the same topology in the plasma membrane (FIG. 2). Both cDNAs are predicted to encode a protein that lacks a cleavable signal sequence (von Heijne, 1983) and contains 7 or 8 potential transmembrane domains. The hamster IBAT also has three potential N-linked glycosylation sites.

EXAMPLE III

FUNCTIONAL CHARACTERIZATION OF THE ILEAL BILE ACID TRANSPORTER

Methods

Cell Culture

[$^3$H] taurocholic acid (2.0–2.6 Ci/mmol) was obtained from Du Pont-New England Nuclear. Unlabeled bile acids were purchased from the Sigma Chemical Co. (St. Louis, Mo.) and CalBiochem (San Diego, Calif.). COS-1 cells were obtained from American Type Culture Collection. RNA molecular weight standards were obtained from Gibco-BRL, (Grand Island, N.Y.).

All cells were grown in monolayer at 37° C. in an atmosphere of 5% $CO_2$. COS cells were maintained in medium A which consisted of Dulbecco's modified Eagle's minimum essential medium containing 4500 mg/L D-glucose, 10% (v/v) fetal calf serum, 100 units/ml penicillin, and 100 μg/ml streptomycin (Gibco, Inc., Grand Island, N.Y.). For bile acid uptake assays, COS cells were switched to medium B which consisted of Dulbecco's modified Eagle's minimum essential medium containing 4500 mg/L D-glucose, 0.2% (w/v) fatty acid-free BSA (Sigma), 100 units/ml penicillin, and 100 μg/ml streptomycin. To analyze the $Na^+$-dependence of bile acid uptake, COS cells were switched to medium C. which contained a modified Hank's balanced salt solution (Chandler et al., 1993), 0.2% (w/v) fatty acid-free BSA (Sigma), 100 units/ml penicillin, and 100 μg/ml streptomycin.

Taurocholate Uptake Assays

A modified [$^3$H] taurocholate uptake assay was used to characterize the IBAT cDNA clone. On day 0, dishes of 1.50×10$^6$ cells per 100-mm dish were plated in medium A. On day 1, the cells were transfected by the DEAE-dextran method (Esser et al., 1988) with 5 μg plasmid DNA. On day 2, the transfected cells were trypsinized, pooled, and replated in 24 well culture plates at 7×10$^4$ cells/well. On day 4, the cells were incubated with medium B or C supplemented with the indicated concentration of [$^3$H] taurocholate. After the indicated amount of time at 37° C., the medium was removed, and each cell monolayer was washed and processed to determine cell-associated protein and radioactivity as described above.

Results $Na^+$-dependent bile acid uptake has been demonstrated in brush border membranes of the kidney (Wilson et al., 1981) and the sinusoidal membranes of the liver (Boyer et al., 1992). In the small intestine, active bile acid transport has been characterized in the ileum but is notably absent from the duodenum and proximal jejunum (Wilson, 1981). To compare IBAT mRNA expression with the known tissue distribution of bile acid transport activity, Northern blot analysis was performed with poly(A)$^+$ RNA from hamster kidney, liver, duodenum, jejunum, and ileum.

It was found that a single message of approximately 4.0 kb was readily detected in hamster ileum and kidney and weakly detectable in hamster jejunum (FIG. 3). No hybridization was observed with mRNA from hamster liver or duodenum, even after prolonged exposure of the blots. Stripping and reprobing the blots with a probe for glyceraldehyde-3-phosphate dehydrogenase (GAPD) (Ercolani et al., 1988) confirmed that equal amounts of RNA were loaded in each lane (FIG. 3, lower panel).

Figure 4:
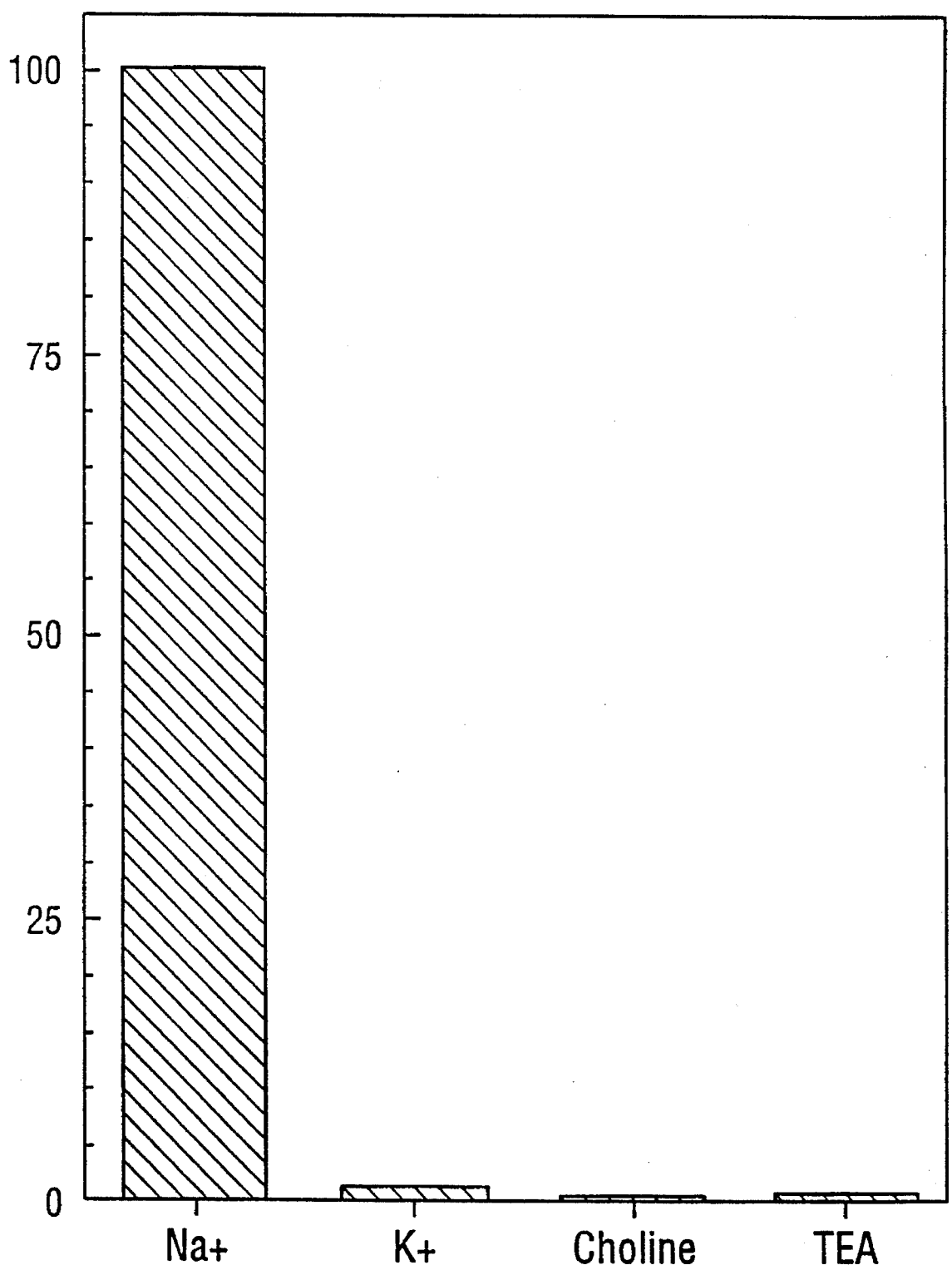
FIG. 4. Sodium-dependence of taurocholate uptake in IBAT-transfected COS cells. On day 0, dishes of 1.50×10$^6$ COS cells per 100-mm dish were plated in medium A. On day 1, cells were transfected with 5 μg of pIBAT or pCMV-βgal plasmid by the DEAE-dextran method. On day 2, each group of transfected cells was trypsinized, pooled, and replated in 24 well culture plates at 7×10$^4$ cells/well. On day 4, the cells were incubated with medium C supplemented with 5 μM [$^3$H] taurocholate (2.0 Ci/mmol) and containing 137 mM sodium or equal concentrations of tetraethylammonium, potassium, or choline. After 15 minutes at 37° C., the medium was removed, and each cell monolayer washed and processed to determine cell-associated protein and radioactivity. Taurocholate uptake in the presence of 137 mM sodium was set at 100% and all values are graphed relative to this level. The "100% of control" value was 134±26 pmoles min$^1$ mg$^1$ protein (n=10).

A critical property of the ileal bile acid transporter is its dependence on an external $Na^+$ gradient (Lack, 1979). To examine IBAT's $Na^+$-dependence, pIBAT-transfected COS cells were incubated in a modified Hanks buffer containing either 137 mM $Na^+$ or equal concentrations of tetraethylammonium (TEA), $K^+$, or choline. It was found that small cations such as $K^+$ or organic cations such as TEA and choline were unable to support [$^3$H] taurocholate uptake (FIG. 4). However, in the presence of $Na^+$, [$^3$H] taurocholate was stimulated over 100-fold.

To examine the kinetics of bile acid uptake by IBAT, transfected COS cells were incubated for 15 minutes with increasing concentrations of [$^3$H] taurocholate. Preliminary studies have shown that transport of 5 μM [$^3$H] taurocholate was linear with time for 30 minutes at 37° C. Transport of [$^3$H] taurocholate by the pIBAT-transfected COS cells exhibited saturable kinetics (FIG. 5A). As determined by Eadie-Hofstee analysis, IBAT exhibited taurocholate uptake activity with an apparent Km of 33 μM and a Vmax of 396 pmol min$^{-1}$ mg$^{-1}$ protein (FIG. 5B).

Figure 6A:
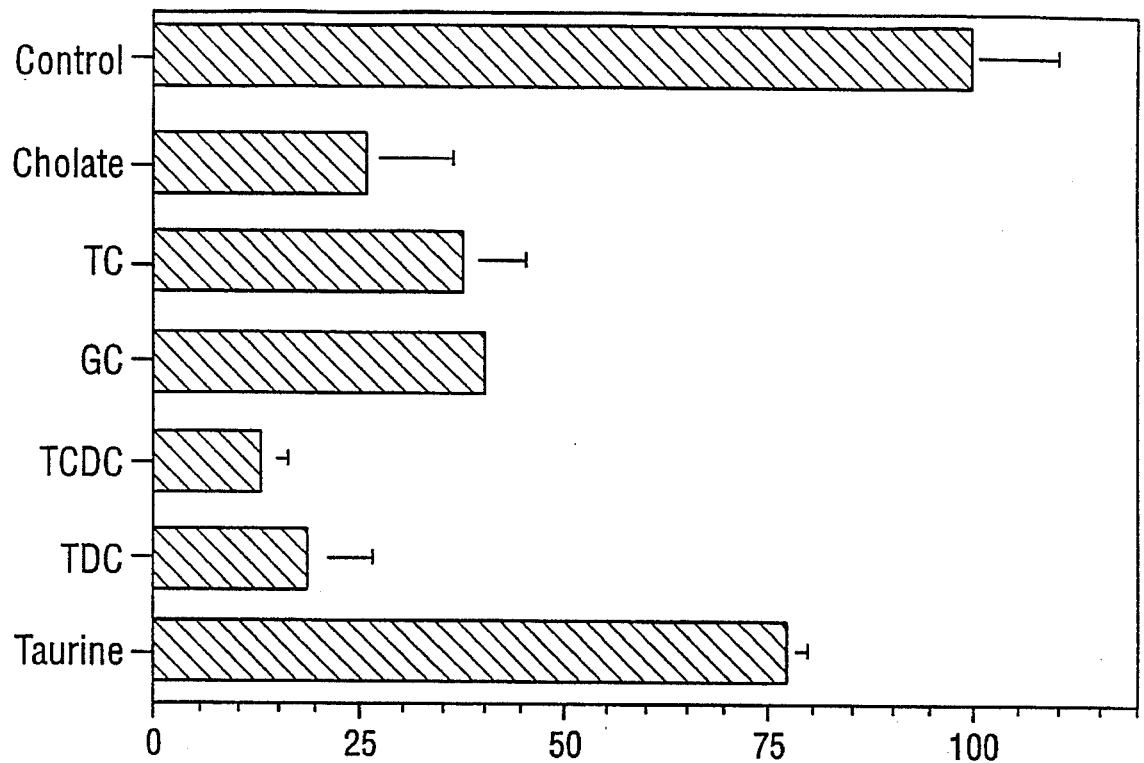
FIG. 6A. Transport specificity of pIBAT-transfected COS cells in the presence of competitors. COS cells were plated and transfected as described in the description of FIG. 4 (immediately above). On day 4, the cells were incubated in medium B supplemented with 5 μM [$^3$H] taurocholate (2.0 Ci/mmol) in the presence or absence of 50 μM unlabeled competitor. TC: taurocholate, GC: glycocholate, TCDC: taurochenodeoxycholate, TDC: taurodeoxycholate. Taurocholate uptake in the absence of competitor was set at 100% and all values are graphed relative to this level. The "100% of control" value was 36.1 ±3.7 pmoles min$^{-1}$ mg$^{-1}$ protein. Each bar represents the mean ± standard deviation (n=6).

To examine the transport specificity of the IBAT protein, COS cells were transfected with the IBAT cDNA and incubated with 50 μM unlabeled bile acid or other competitor. At a 10-fold molar excess of unlabeled bile acid, [$^3$H] taurocholate uptake was inhibited 87% with taurochenodeoxycholate, 80% with taurodeoxycholate, 63% with taurocholate, 61% with glycocholate, and 51% with cholate, whereas the unlabeled amino acid taurine had a limited effect (FIG. 6A). At equal concentrations, the dihydroxy bile acids (taurochenodeoxycholate and taurodeoxycholate) competed more effectively for [$^3$H] taurocholate uptake than unlabeled taurocholate, a trihydroxy bile acid.

Figure 6B:
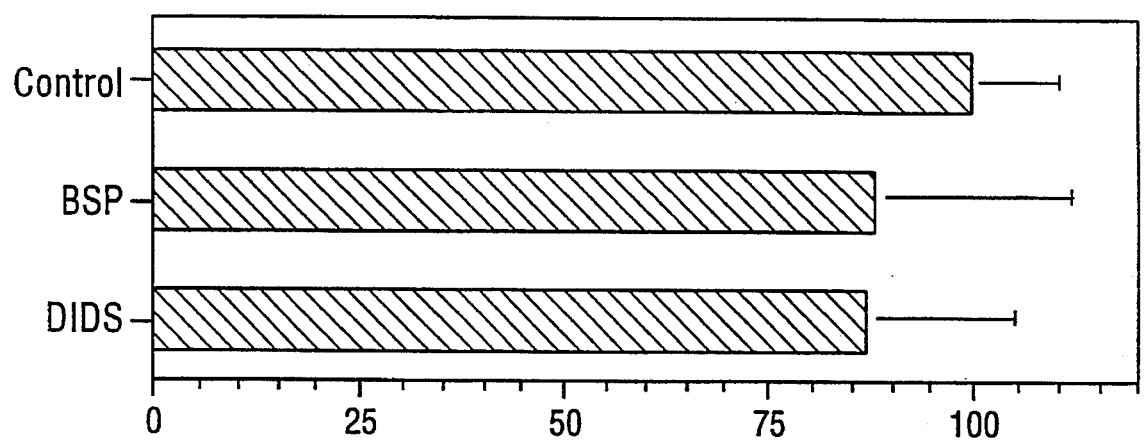
FIG. 6B. Transport specificity of pIBAT-transfected COS cells in the presence of inhibitor. COS cells were plated and transfected as described in the description of FIG. 4 (immediately above). On day 4, the cells were incubated in medium B supplemented with 5 μM [$^3$H] taurocholate (2.0 Ci/mmol) in the presence or absence of 100 μM unlabeled inhibitor. Taurocholate uptake in the absence of inhibitor was set at 100%, as described in the description of FIG. 6A (immediately above), and all values are graphed relative to that level. The "100% of control" value was 90.7 ±11.9 pmoles min$^{-1}$ mg$^{-1}$ protein. Each bar represents the mean ± standard deviation (n=6).

Cholephilic organic compounds such as bromosulfophthalein (BSP) and the bifunctional anion transport inhibitor 4,4'-diisothiocyano-2,2'-disulfonic acid stilbene (DIDS) have been shown to inhibit $Na^+$-dependent taurocholate uptake by liver membranes (Zimmerli et al., 1989) but not ileal brush border membranes (Kramer et al., 1992). Uptake of [$^3$H] taurocholate by pIBAT-transfected COS cells was determined not to be significantly inhibited by the addition of BSP or DIDS (FIG. 6B).

EXAMPLE IV

USE OF NUCLEIC ACID SEGMENTS TO ISOLATE FULL LENGTH GENOMIC SEQUENCES

The nucleic acid sequences of the present invention may be used to isolate the full length genomic sequences encoding the ileal/renal bile acid transporters and surrounding control regions. A genomic library could be constructed by well known techniques such as those taught in Sambrook et al., (1989). For example, genomic DNA may be isolated from the hamster or human ileal tissue and partially digested with a restriction enzyme such as Sau 3A. The digested DNA would then be packaged in a lambda vector by the use of the Packagene system (Promega) for example. This library could then be screened analogously to the expression screening of the cDNA library described in Example I. Alternatively, the genomic clones could be transferred to a solid substrate such as a nitrocellulose filter and hybridized to labeled nucleic acid sequences of the present invention in order to select for the bile acid cotransporter genes.

It is understood that because of interspecies homology, the nucleic acid segments of the present invention will also be useful to isolate the genomic sequences or even cDNA sequences from other species of mammals. The nucleic acid segments of the present invention of any size up to and including the entire sequence designated as seq id no: 1 or seq id no: 3 could be labelled and used as a probe to isolate the genomic sequences, including the intron sequences and control sequences for gene expression of the ileal/renal bile acid cotransporter. An important use of this sequence information would be to determine whether the ileal and renal genes are controlled by similar promoter/enhancer elements or whether there are tissue specific differences. This would enable the targeting of activators/repressors to specific tissues. The isolation of the promoter regions will also allow the screening of candidate substances as activators or inhibitors of genetic expression of the bile acid cotransporters.

In order to identify the desired genomic sequences, the individual clones could be separated, for example by polyacrylamide gel electrophoresis, or agarose gel electrophoresis and then transferred to a filter such as a nitrocellulose filter or any other suitable material. The nucleic acid probe would then be labelled with $^{32}$P by enzymatic labelling with polynucleotide kinase, for example. The clone could also be radioactively labelled by nick translation or in a polymerase chain reaction that included radio-labeled nucleotides. Alternatively, the probe could be labelled with a fluorescent marker such as biotin or any fluorophore. Such labelling techniques are well known in the art.

The labelled probe would then be hybridized to the denatured DNA on the filter and washed under increasingly stringent conditions, incrementally higher temperatures for example, until the positive clones can be identified by autoradiography or by fluorescence. These positive clones would then be rescreened and sequenced to determine the full gene sequence encoding the ileal/renal bile acid cotransporter protein.

The full protein could then be expressed in an *E. coli* strain, for example, and used for further analysis. It is understood that the protein could also be truncated or altered by site directed mutagenesis, for example and that such altered proteins or partial sequences would also fall within the scope of the present invention.

EXAMPLE V

PRODUCTION OF ANTIBODIES

A synthetic peptide (obtained from Research Genetics, San Diego, Calif.) corresponding to amino acids 335–348 (SEQ ID NO: 5) of the hamster ileal Na$^+$/bile acid cotransporter was coupled to tuberculin purified protein derivative (PPD; Statens Seruminstitut, Copenhagen, Denmark) using glutaraldehyde. Three New Zealand White rabbits were immunized with 500 μg of coupled peptide in Freund's complete adjuvant. Rabbit serum was assayed by immunoblot analysis for anti-ileal bile acid transporter antibody using bile acid transporter-transfected COS cell extracts as well as ileal brush border membrane. To demonstrate the specificity of the antibody, 100 μg of rat jejunal or ileal brush border membrane protein was denatured and reduced in Laemmli sample buffer containing 2% (w/v) SDS and 2.5% (v/v) β-mercaptoethanol. The protein was then subjected to electrophoresis on a 10% SDS-polyacrylamide gel and either stained with coomassie blue ("Coomassie") or transferred to a nitrocellulose filter ("Immunoblot"). See FIG. 7. The nitrocellulose filter was incubated with 1.8 μg/ml of rabbit antipeptide lgG directed against amino acids 335–348 (SEQ ID NO: 5) of the hamster ileal bile acid transporter. To visualize the primary antibody, the filter was incubated with alkaline phosphatase-conjugated goat antirabbit lgG(l: 2500 dilution; BioRad, cat no. 170-6518). The position of molecular weight markers run in adjacent lanes were determined by staining the nitrocellulose filter with ponceau S prior to blocking the filter with Blotto.

EXAMPLE VI

ISOLATION OF HUMAN ILEAL/RENAL BILE ACID TRANSPORTER cDNA

The polymerase chain reaction was used to derive an unambiguous probe for cDNA screens and to characterize hybridizing lambda phage clones. Oligonucleotides corresponding to amino acids 75 to 81 and 260 to 267 of the hamster ileal bile acid transporter were used in a polymerase chain reaction to derive an unambiguous probe for cDNA library screens. The polymerase chain reaction was performed with approximately 100 ng of first strand human ileal cDNA and 50 pmoles of primers. The reaction mixture was boiled, after which PCR was carried out sequentially for 1 min at 94° C., 2 min at 45° C., and 3 min at 72° C. with Taq polymerase for 35 cycles. The specific 576 bp PCR product was resolved on a 1% agarose gel, eluted from the gel slice and subcloned into the vector pT7Blue (Novagen, Madison, Wis.). After sequencing the PCR product in the pT7Blue vector, the PCR insert corresponding to amino acids 76 to 267 of the human ileal/renal bile acid transporter was excised from the pT7Blue plasmid using Eco R1 and Hind III. The isolated insert was uniformly labeled with $^{32}$p by the random-hexamer labeling procedure.

Plaques (1.2×10$^6$) from a human ileal cDNA library were screened using the $^{32}$P-labeled probe derived from the polymerase chain reaction product. Filters were hybridized at 42° C. in 50% formamide containing 1×10$^6$ cpm/ml of hybridization probe and washed in 0.2×SSC (1×SSC=150 mM sodium chloride and 15 mM sodium citrate, pH 7) and 0.5% SDS at 60° C. Seven positive clones were obtained and characterized. Two of the positive clones, designated pH60 and pH13, each of which encoded part of the gene were fused to make a single clone encoding the entire gene. This clone was designated as pHIBAT and was used for subsequent studies. Phage DNA was prepared and cDNA inserts were subcloned into pBluescript KSII vectors for restriction mapping and DNA sequencing. The human cDNA genetic sequence is designated herein as SEQ ID NO: 3 and the derived amino acid sequence is designated SEQ ID NO: 4.

EXAMPLE VII

DETECTION OF MUTANT ALLELE IN HUMAN PATIENT

To demonstrate the general utility of the invention, the human ileal bile acid transporter cDNA clone was used to identify a point mutation which inactivates the ileal bile acid transporter in a patient with Crohn's disease.

The patient, a 27 year old white female, complained of midabdominal pain, loose stools, and weight loss for one year. Results from an upper GI exam and colonoscopy revealed irregularities in the terminal ileum consistent with Crohn's disease. She was referred for exploratory laparotomy and bowel resection. Following resection of the inflamed region of the terminal ileum, the resected sample was sent to pathology where a biopsy was removed. The biopsy was used to construct a cDNA library in the vector lambda gt10. The library was screened using a $^{32}$P-labeled probe derived from the human ileal/renal bile acid transporter. In this particular example, an entire cDNA clone of the human ileal bile acid transporter gene was labeled and used as the probe. Filters were hybridized at 42° C. in 50% formamide containing 1×10$^6$ cpm/ml of hybridization probe and washed in 0.2×SSC (1×SSC=150 mM sodium chloride and 15 mM sodium citrate, pH 7) and 0.5% SDS at 60° C. Phage DNA from the positive clones was prepared and cDNA inserts were subcloned into pBluescript KSII vectors for restriction mapping and DNA sequencing. A single nucleotide change was detected at codon 290 of the predicted coding sequence. The C-to-T transition changed the predicted amino acid from the normal proline residue to a serine.

Figure 9:
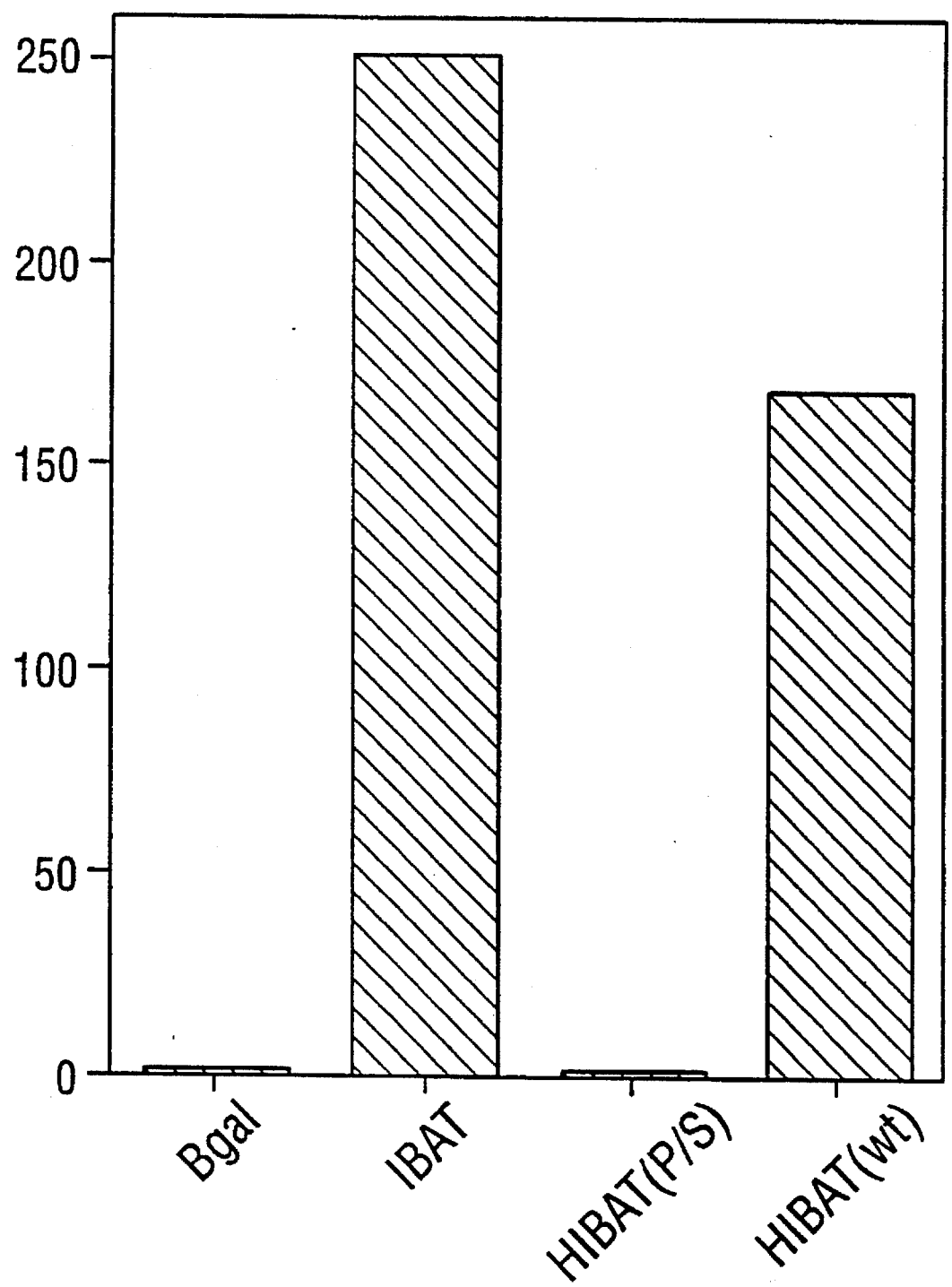
FIG. 9. Taurocholate uptake in human ileal bile acid transporter-transfected COS cells: Effect of a naturally occurring mutation at amino acid 290. On day 0, dishes of $5 \times 10^5$ COS cells/60 mm dish were plated in DMEM (HG) containing 10% (v/v) fetal calf serum, 100 units/ml penicillin and 100 µg/ml streptomycin. On day 1, cells were transfected by the DEAE-dextran method with 2 µg of either pCMV-βgal, pCMX-IBAT, pCMV-HIBAT(P/S) encoding a serine at position 290, or pCMV-HIBAT which encodes a proline residue at position 290. On day 4, the cells were incubated with a modified Hanks balanced salt solution containing 5 µM [$^3$H] taurocholate (2.1 Ci/mmol) and 0.2% (w/v) bovine serum albumin. After incubating for 15 min. at 37° C., the medium was removed and the cell monolayer was washed five times with ice-cold phosphate-buffered saline plus 0.2% (w/v) bovine serum albumin and then once with ice-cold phosphate-buffered saline alone. Cell monolayers were lysed in 0.1 N NaOH and aliquots were taken to determine cell-associated protein and radioactivity. The data is reported as [$^3$H] taurocholate uptake relative to pCMV-βgal transfected COS cells.
Figure 10:
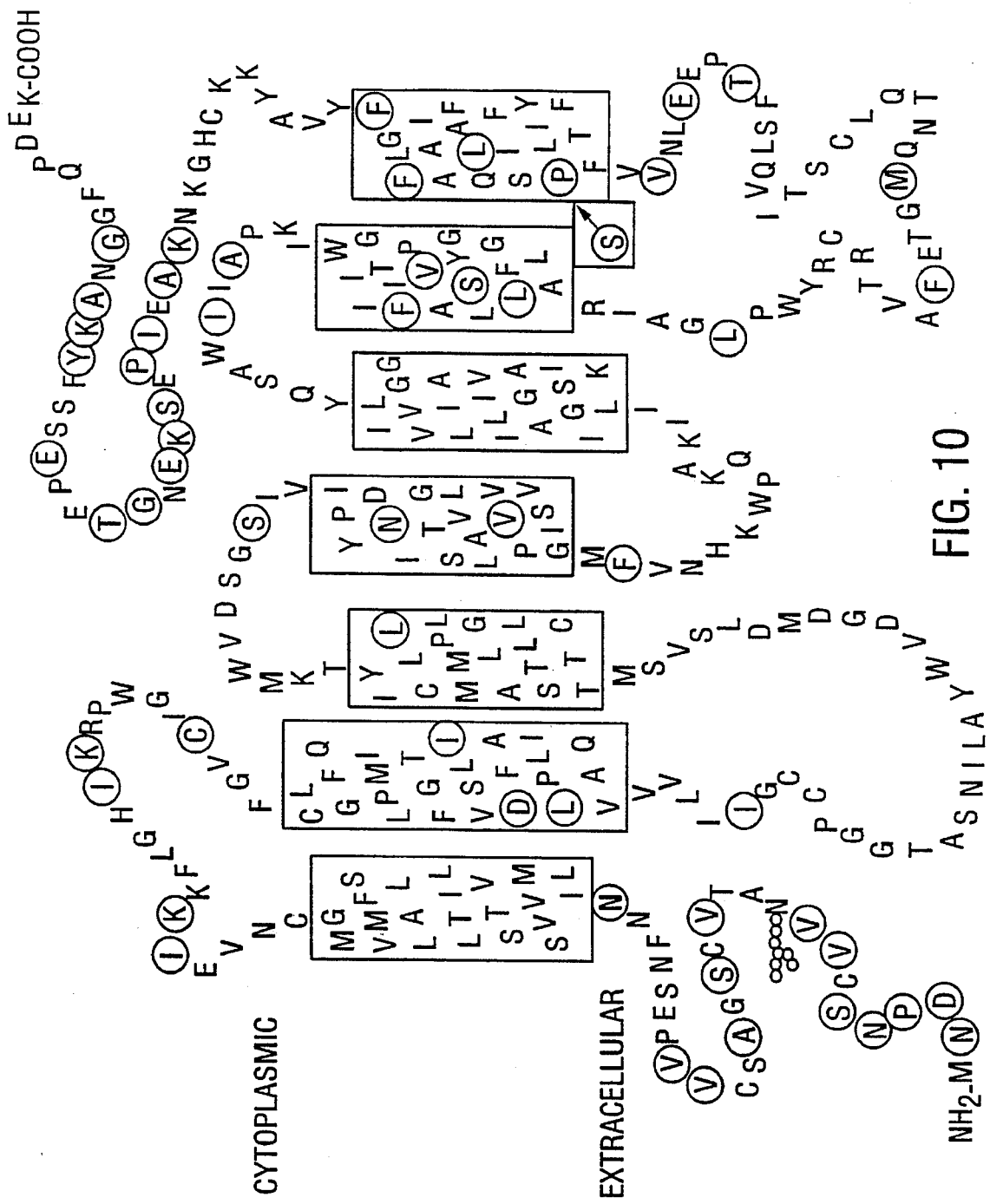
FIG. 10. Topology model for the human ileal/renal bile acid transporter. The deduced amino acid sequence (seq id no: 4) and predicted secondary structure for the human ileal/renal bile acid transporter is shown. The circled residues are those which differ between the human (seq id no: 4) and hamster (seq id no: 2) bile acid transporter amino acid sequences. The boxed residues represent predicted transmembrane domains I through VII. The small circles represent a potential N-linked glycosylation site. The serine substitution for a proline at position 290 is indicated by a box and arrow.

To assess the functional significance of such a change, the cDNA insert containing the entire coding sequence were subcloned into the expression plasmid, pCMV5 for transfection studies. As shown in FIG. 9, the normal human ileal/renal bile acid transporter was able to actively take up bile acids following transfection into COS cells, whereas the bile acid transporter with the proline to serine mutation at position 290 was completely inactive. Analysis of the ileal/renal bile acid transporter protein expressed in the transfected cells revealed that approximately equal amounts of protein were expressed. Therefore, even though the mutant ileal/renal bile acid transporter was competent for protein expression, the expressed protein was unable to transport bile acids. Additional screening of the library constructed from the patient identified 2 additional clones encoding serine at position 290, and 2 additional clones encoding proline at position 290. This suggests that the patient is heterozygous for the ileal/renal bile acid transporter mutation. The probes used to discover the mutation are also useful in analyzing the inheritance of the proline to serine 290 mutation in related family members and in understanding the relationship between the mutation and the pathogenesis of Crohn's disease.

EXAMPLE VIII

INHIBITION OF BILE ACID TRANSPORTER

Bile acids are synthesized from cholesterol in the liver. This process is tightly regulated to maintain the proper bile acid pool size. If the pool expands, bile acid synthesis decreases, whereas if the pool contracts, more cholesterol is converted to bile acids. Following their synthesis, bile acids are secreted into the small intestine where they act to facilitate fat absorption. Bile acids are then taken up by a specific transporter in the distal small intestine, secreted into the portal circulation, and transported into the liver for resecretion into bile. This process is extremely efficient; only about 5% of the total bile acid escapes reabsorption in the intestine and is lost in the stool. In man, this represents a major route for the elimination of cholesterol (the precursor to bile acids) and has been exploited for many years as a means of lowering plasma cholesterol levels. This approach involves the use of nondigestible charged resins which, when ingested, bind up bile acids in the small intestine and block their reabsorption. This approach requires that the patient consume substantial quantities (15–30 g/day) of the bile acid-sequestrants several times a day. Common side effects include nausea, bloating, constipation and intestinal blockage. As a result, patient compliance is poor and this therapy has met with mixed success.

An alternative strategy would be to directly inhibit the intestinal bile acid transporter. Several strategies are now possible with the use of the present invention. For example, naturally occurring inhibitors may be found with the screening methods disclosed herein. Alternatively, inhibitors may be designed, based on the predicted structure of the cotransporter protein made possible by the amino acid sequences disclosed herein. Another alternative would be antisense and ribozyme technology based on the nucleic acid sequences of the present invention. For example, oligonucleotides complementary to the mRNA sequence of the cotransporter gene could be targeted to the ileal tissues to interfere with translation and thus expression of the cotransporter.

EXAMPLE IX

TREATMENT OF CIRRHOSIS

In patients with liver cirrhosis, primary biliary cirrhosis, sclerosing cholangitis and other diseases which block the normal secretion of bile acids by the liver, bile acids accumulate in the liver and systemic circulation. While not a direct cause of the disease, the accumulation of bile acids is associated with the symptoms and progression of the disease. In these patients, the liver continues to degenerate, eventually leading to liver failure and death. Current treatment for this cholestasis includes the administration of a naturally-occurring, but low abundance bile acid, Ursodeoxycholic acid (UDCA). UDCA is believed to act by promoting the movement of cytotoxic bile acids from the liver into the systemic circulation. This treatment improves liver function, but does not stop the progression of the disease. As an alternative, liver transplant is an effective, but very expensive treatment. Unfortunately, even though a majority of liver transplants are performed to treat these disorders, the cost of the procedure and shortage of liver donors limits its usefulness.

An alternative treatment strategy would be to directly inhibit the kidney bile acid transporter which reabsorbs bile acids in the renal tubules. This is predicted to increase elimination of cytotoxic bile acids from the body via the urine. The bile acid transporter's sequence as disclosed herein will allow the discovery of suitable reagents to aid in the design of inhibitors. The currently available technology to screen for inhibitors is to use intact laboratory animals, or laboratory animal kidney sections. However, this strategy is technically cumbersome, limited to small numbers of compounds, and expensive. The renal bile acid cotransporter may be inhibited in a similar way to the ileal bile acid cotransporter as described in Example VIII, supra.

EXAMPLE X

TREATMENT OF CHRONIC DIARRHEA

Chronic diarrhea is a serious clinical problem whose cause may remain elusive even after complete diagnostic examination. One possible pathophysiologic mechanism for diarrhea in these patients is malabsorption of bile acids by the ileum. It is well accepted that ileal resection or ileal disease can result in malabsorption of bile acids and that unabsorbed bile acids can induce a watery diarrhea in those patients. However, the issue of the contribution of bile acid malabsorption to the pathogenesis of diarrhea has not been resolved with the currently available diagnostic tests.

One possibility is that the ileal bile acid transporter gene itself is defective or aberrantly down-regulated in patients with chronic idiopathic diarrhea. The sequences of the present invention can be used for diagnosis through the creation of antibodies and DNA probes that target regions of mutation responsible for the disfunction. In other embodiments, gene therapy may be possible using the nucleic acid sequences of the present invention to promote normal cotransporter function.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Andersson, S., Davis, D. L., Dahlback, H., Jornvall, H., and Russell, D. W. (1989) *J. Biol. Chem.* 264, 8222–8229.

Baldwin, J. M. (1993) EMBO J. 12, 1693–1703.

Barnard, J. A., and Grishan, F. K. (1987) *Gastroenterology* 93, 925–933.

Blobel, G., and Dobberstein, B. (1975) *J. Cell Biol.* 67, 852–862.

Boyer, J. L., Graf, J., and Meier, P. J. (1992) *Ann. Rev. Physiol.* 54, 415–438.

Briggs, M. S., Yokoyama, C., Wang, X., Brown, M. S. and Goldstein, J. L. (1993) *J. Biol. Chem.* 268, 14490–14496.

Buchwald, H., Varco, R. L., Matts, J. P. et al. (1990) *N. Enl. J. Med.* 323, 946–955.

Chandler, C. E., Zaccaro, L. M., and Moberly, J. B. (1993) *Am. J. Physiol.* 27, G1118–G1125.

Chirgwin, J. M., Przybyla, A. E., MacDonald, and Rutter, W. J. (1979) *Biochemistry* 18, 5294–5299.

Church, G. M., and Gilbert, W. (1984) *Proc. Natl. Acad. Sci. U.S.A.* 81, 1991–1995.

The Cold Spring Harbor Manual for Hybridoma Development

DeGrip, W. J. (1982) *Methods Enzymol* 81, 197–207.

Davis, S., Aldrich, T. H., Valenzuela, D. M., Wong, V., Furth, M. E., Squinto, S. P., and Yancopoulos, G. D. (1991) *Science* 253, 59–63.

Deguchi, Y., Yamamoto, I., and Anraku, Y. (1990) *J. Biol. Chem.* 265, 21704–21708.

Devereux, J., Haeberli, P., and Smithies, 0. (1984) *Nucl. Acids Res.* 12, 387–395.

Dietschy, J. M. (1968) *J. Lipid Res.* 9, 297–309.

Ercolani, L., Florence, B., Denaro, M., and Alexander, M. (1988) *J. Biol. Chem.* 263, 15335–15341.

Esser, V., Limbird, L. E., Brown, M. S., Goldstein, J. L., and Russell, D. W. (1988) *J. Biol. Chem.* 264, 8222–8229.

Fliesler, S. J. and Basinger, S. F. (1985) *Proc. Natl. Acad. Sci. U.S.A.* 82, 1116–1120.

Fricker, G., Kramer, W., Buscher, H.-P., Gerok, W., and Kurz, G. (1982) *Hopp Seylers Z Physiol Chem* 363, 897–905.

Gong, Y. -Z., Zwarych, P. P., Lin, M. C. and Wilson F. A. (1991) Biochem. Biophys. Res. Comm. 179, 204–209.

Goodman, D. S. and the Expert Panel on Detection, Evaluation and Treatment of High Blood Cholesterol in Adults (1988) NIH Publication No. 88-2925.

Hagenbuch, B., Stieger, B., Foguet, M., Lubbert, H., and Meier, P. J. (1991) *Proc. Natl. Acad. Sci. U.S.A.* 88, 10629–10633.

Harlow, E. and D. Lane, *Antibodies "A Laboratory Manual,"* Cold Spring Harbor Laboratory, 1988

Heubi, J. E., Balistreri, W. F., Fondacaro, J. P., Partin, J. C. and Schubert, W. K. (1982) *Gastroenterology* 83, 804–811.

Hofmann, A. F. (1977) *Clinics in Gastroenterology* 63, 3–24.

Hofmann, A. F. (1989) in *Gastrointestinal Disease*, pp. 144–161.

Jacquemin, E., Hagenbuch, B., Steiger, B., Wolkoff, A. W. and Meier, P. J. (1992) *Hepatology* 16, 89A.

Khorana, H. G. (1992) *J. Biol. Chem.* 267, 1–4.

Kozak, M. (1987) *Nucl. Acids Res.* 15, 8125–8148.

Krag, E. and Phillips, S. F. (1974) *J. Clin. Invest.* 53, 1686–1694.

Kramer, W., Burckhardt G., Wilson, F. A. and Kurz, G. (1983) *J. Biol. Chem.* 258, 3623–3627.

Kramer, W., Nicol, S-B., Girbig, F., Gutjahr, U., Kowalewski, S., and Fasold, H. (1992) *Biochim. Biophys. Acta* 1111, 93–102.

Kyte, J., and Doolittle, R. F. (1982) *J. Mol. Biol.* 157, 105–132.

Lack, L. and Weiner, I. M. (1961) *Am. J. physiol.* 200, 313–317.

Lack, L. (1979) *Environ. Health Perspect.* 33, 79–90.

Lewis, M. C., and Root, C. (1990) *Am. J. Physiol.* 259, G233–238.

Lin, M. C., Weinberg, S. L., Kramer, W., Burckhardt, G. and Wilson, F. A. (1988) *J. Membr. Biol.* 106, 1–11.

Lin, M. C., Kramer, W., and Wilson, F. A. (1990) *J. Biol. Chem.* 265, 14986–14995.

Marcus, S. N., Schteingart, C. D., Marquez, M. L., Hofmann, A. F., Xia, Y., Steinbach, J. H., Ton-Nu, H-T., Lillienau, J., Angellotti, M. A., and Schmassmann, A. (1991) *Gastroenterology* 100, 212–221.

Mullins, J. G. L., Beechey R. B., Gould G. W., Campbell, F. C., and Shirazi-Beechey, S. P. (1992) *Biochem. J.* 285, 785–790.

Read, N. W., Krejs, G. J., Read, M. G., Santa Ana, C. A., Morawski, S. G. and Fordtran, J. S. (1980) *Gatroenterology* 78, 264–271.

Russell, D. W., and Setchell, K. D. R. (1992) *Biochemistry* 31, 4737–4749.

Saiki, R. K., Gelfand, D. H., Stoffel, S., Scharf, S. J., Higuchi, R., Horn, G. T., Mullis, K. B., and Erlich, H. A. (1988) *Science* 239, 487–491.

Sambrook, J., Fritsch, E. F., and Maniatis, T. (1989) *Molecular Cloning: A Laboratory Manual*, Cold Spring Harbor Laboratory, Cold Spring Harbor, N.Y.

Schiff, E. R., Small, N. C., and Dietschy, J. M. (1972) *J. Clin. Invest.* 51, 1351–1362.

Schwenk, M., Hegazy, E., and Lopez del Pino, V. (1983) *Eur. J. Biochem.* 131, 387–391.

Sorscher, S., Lillienau, J., Meinkoth, J. L., Steinbach, J. H., Scheingart, C. D., Feramisco, J., and Hofmann, A. F. (1992) *Biochem Biophys. Res. Comm.* 186, 1455–1462.

U.S. Pat. No. 4,196,265

U.S. Pat. No. 4,603,102

Von Dippe, P., Amoul, M. and Levy, D. (1993) *Am. J. Physiol.* 264, G528–G534.

von Heijne, G. (1983) *Eur. J. Biochem.* 133, 17–21.

Weinberg, S. L, Burckhardt, G., and Wilson, F. A. (1986) *J. Clin. Invest.* 78, 44–50.

Weiner, I. M., Glasser, J. E., and Lack, L. (1964) *Am. J. Physiol.* 207, 964–970.

Wilson, F. A. and Dietschy, J. M. (1974) *Biochim. Biophys. Acta* 363, 112–126.

Wilson, F. A. and Treanor, L. L. (1979) *Biochim. Biophys. Acta* 554, 430–440.

Wilson, F. A. (1981) *Am. J. Physiol.* 241, G83–92.

Wilson, F. A., Burckhardt, G., Murer, H., Rumrich, G., and Ullrich, K. J. (1981) *J. Clin. Invest.* 67, 1141–1150.

Wright, E. M., Hager K. M., and Turk E. (1992) *Curr. Opinion Cell Biol.* 4, 696–702.

Zimmerli, B., Valantinas, J., and Meier, P. J. (1989) *J. pharmacol. Exp. Ther.* 250, 301–308.

---

What is claimed is:

1. An isolated DNA segment wherein said segment encodes a mammalian ileal/renal bile acid cotransporter having an amino acid sequence in accordance with seq id no:2 or seq id no:4.

2. The DNA segment of claim 1, wherein the DNA segment has the nucleic acid sequence of seq id no: 1 or seq id no: 3.

3. The DNA segment of claim 1, wherein the DNA segment is positioned under the control of a promoter.

4. The DNA segment of claim 3, wherein the DNA segment is positioned under the control of a heterologous promoter.

5. A recombinant vector comprising the DNA segment of claim 1.

6. A recombinant host cell comprising a vector in accordance with claim 5.

7. The recombinant host cell of claim 6, wherein the host cell is a prokaryotic cell.

8. The recombinant host cell of claim 6, wherein the host cell is a eukaryotic cell.

9. The recombinant host cell of claim 6, wherein the recombinant vector is an expression vector and the host cell expresses an ileal/renal bile acid cotransporter polypeptide.

10. The recombinant host cell of claim 9, wherein the recombinant expression vector comprises a nucleic acid sequence in accordance with the nucleic acid sequence set forth in seq id no: 1 or seq id no: 3.

11. A recombinant vector, wherein the vector comprises a nucleic acid sequence in accordance with the nucleic acid sequence set forth in seq id no: 1 or seq id no: 3.

12. The recombinant vector of claim 11, wherein the vector is a recombinant expression vector capable of expressing an ileal/renal bile acid transporter polypeptide on introduction into a host cell.

13. The recombinant vector of claim 11, wherein the nucleic acid sequence set forth m SEQ ID NO:1 or SEQ ID NO:3 has been inserted into a vector selected from the group consisting of pCMX and pCMV5.

14. An isolated nucleic acid segment which comprises a nucleic acid fragment, wherein said fragment consists of at least a 17 nucleotide long stretch which corresponds to the coding region of the nucleic acid sequence of seq id no:1 or seq id no:3.

15. The nucleic acid segment of claim 14, wherein said fragment consists of at least a 30 nucleotide long stretch which corresponds to the coding region of the nucleic acid sequence of seq id no:1 or seq id no:3.

16. The nucleic acid segment of claim 15, wherein said fragment consists of at least a 50 nucleotide long stretch which corresponds to the coding region of the nucleic acid sequence of seq id no:1 or seq id no:3.

17. The nucleic acid segment of claim 16, wherein said fragment consists of at least a 100 nucleotide long stretch which corresponds to the coding region of the nucleic acid sequence of seq id no:1 or seq id no:3.

18. The nucleic acid segment of claim 17, wherein said fragment consists of at least a 1000 nucleotide long stretch which corresponds to the nucleic acid sequence of seq id no:1 or seq id no:3.

19. The nucleic acid segment of claim 18, further defined as comprising a nucleic acid fragment consisting of a 2263 nucleotide long sequence which corresponds to the nucleic acid sequence of seq id no:1.

20. The nucleic acid segment of claim 18, further defined as comprising a nucleic acid fragment, wherein said fragment consists of at least a 1047 nucleotide long stretch which corresponds to seq id no:3.

21. An isolated nucleic acid segment having the nucleic acid sequence of SEQ ID NO:1.

22. An isolated nucleic acid segment having the nucleic acid sequence of SEQ ID NO:3.

* * * * *

UNITED STATES PATENT AND TRADEMARK OFFICE
CERTIFICATE OF CORRECTION

PATENT NO. : 5,589,358
DATED : December 31, 1996
INVENTOR(S) : Paul A. Dawson

It is certified that error appears in the above-indentified patent and that said Letters Patent is hereby corrected as shown below:

In claim 13, column 47, line 6, please delete the letter "m" and insert therefor the word ---in--.

Signed and Sealed this

Twelfth Day of August, 1997

Attest:

BRUCE LEHMAN

Attesting Officer    Commissioner of Patents and Trademarks

UNITED STATES PATENT AND TRADEMARK OFFICE
CERTIFICATE OF CORRECTION

PATENT NO. : 5,589,358

DATED : December 31, 1996

INVENTOR(S) : Paul A. Dawson

It is certified that error appears in the above-identified patent and that said Letters Patent is hereby corrected as shown below:

On the title page, please insert -- [73] Assignee: Wake Forest University
                                                                        Winston-Salem, NC --

Signed and Sealed this

Twenty-seventh Day of January, 1998

Attest:

BRUCE LEHMAN

Attesting Officer        Commissioner of Patents and Trademarks

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 2263 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 109..1152

( x i ) SEQUENCE DESCRIPTION: SEQ ID NO:1:

```
GGTTTAAAAG TTTGACGTGC TCACCAGGTG CTACTCAGCT GCCAGTGGGT AGAGAACCGA            60

GGACAGGTGC TTCTGTGGGG CTTGACTGTT TACACAGCAC AGCCAGAG ATG GAT AAC          117
                                                    Met Asp Asn
                                                     1

TCC TCC ATC TGC AAC CCC AAC GCG ACC ATC TGC GAA GGC GAC TCC TGC          165
Ser Ser Ile Cys Asn Pro Asn Ala Thr Ile Cys Glu Gly Asp Ser Cys
     5              10                  15

ATA GCA CCG GAG AGC AAC TTC AAC GCC ATC CTC AGC GTG GTG ATG AGC          213
Ile Ala Pro Glu Ser Asn Phe Asn Ala Ile Leu Ser Val Val Met Ser
20              25                  30                   35

ACC GTG CTC ACA ATC CTC CTA GCC TTG GTG ATG TTT TCC ATG GGG TGC          261
Thr Val Leu Thr Ile Leu Leu Ala Leu Val Met Phe Ser Met Gly Cys
                 40                  45                  50

AAT GTG GAA CTC CAC AAG TTT CTG GGA CAC CTA AGG CGG CCA TGG GGC          309
Asn Val Glu Leu His Lys Phe Leu Gly His Leu Arg Arg Pro Trp Gly
             55                  60                  65

ATC GTC GTG GGC TTC CTC TGT CAG TTT GGA ATC ATG CCT CTC ACA GGT          357
Ile Val Val Gly Phe Leu Cys Gln Phe Gly Ile Met Pro Leu Thr Gly
         70                  75                  80

TTC GTC CTG TCC GTG GCC TTT GGC ATC CTC CCA GTG CAA GCT GTG GTG          405
Phe Val Leu Ser Val Ala Phe Gly Ile Leu Pro Val Gln Ala Val Val
     85                  90                  95
```

| | | | | | | | | | | | | | | | | |
|---|---|---|---|---|---|---|---|---|---|---|---|---|---|---|---|---|
| GTG | CTG | ATC | CAG | GGT | TGC | TGC | CCT | GGA | GGA | ACT | GCC | TCC | AAT | ATC | CTA | 453 |
| Val 100 | Leu | Ile | Gln | Gly | Cys 105 | Cys | Pro | Gly | Gly | Thr 110 | Ala | Ser | Asn | Ile | Leu 115 | |
| GCC | TAT | TGG | GTA | GAT | GGC | GAC | ATG | GAC | CTC | AGC | GTT | AGC | ATG | ACC | ACC | 501 |
| Ala | Tyr | Trp | Val 120 | Asp | Gly | Asp | Met | Asp 125 | Leu | Ser | Val | Ser | Met 130 | Thr | Thr | |
| TGC | TCC | ACG | CTG | CTT | GCC | CTT | GGA | ATG | ATG | CCC | CTT | TGC | CTC | TTC | ATC | 549 |
| Cys | Ser | Thr | Leu 135 | Leu | Ala | Leu | Gly | Met 140 | Met | Pro | Leu | Cys | Leu 145 | Phe | Ile | |
| TAT | ACC | AAG | ATG | TGG | GTT | GAC | TCA | GGG | ACG | ATT | GTG | ATT | CCT | TAT | GAC | 597 |
| Tyr | Thr | Lys 150 | Met | Trp | Val | Asp | Ser 155 | Gly | Thr | Ile | Val | Ile 160 | Pro | Tyr | Asp | |
| AGC | ATT | GGC | ACT | TCT | CTG | GTT | GCT | CTT | GTT | ATT | CCT | GTT | TCC | ATT | GGA | 645 |
| Ser | Ile 165 | Gly | Thr | Ser | Leu | Val 170 | Ala | Leu | Val | Ile | Pro 175 | Val | Ser | Ile | Gly | |
| ATG | TAT | GTG | AAT | CAC | AAA | TGG | CCC | CAA | AAA | GCA | AAG | ATC | ATA | CTT | AAA | 693 |
| Met 180 | Tyr | Val | Asn | His | Lys 185 | Trp | Pro | Gln | Lys | Ala 190 | Lys | Ile | Ile | Leu | Lys 195 | |
| ATT | GGA | TCC | ATC | GCA | GGT | GCA | ATT | CTC | ATT | GTT | CTC | ATC | GCT | GTG | GTT | 741 |
| Ile | Gly | Ser | Ile | Ala 200 | Gly | Ala | Ile | Leu | Ile 205 | Val | Leu | Ile | Ala | Val 210 | Val | |
| GGA | GGA | ATA | CTG | TAC | CAA | AGT | GCC | TGG | ACC | ATT | GAA | CCC | AAG | CTG | TGG | 789 |
| Gly | Gly | Ile | Leu | Tyr 215 | Gln | Ser | Ala | Trp | Thr 220 | Ile | Glu | Pro | Lys | Leu 225 | Trp | |
| ATT | ATA | GGA | ACC | ATA | TAT | CCT | ATA | GCT | GGC | TAC | GGC | CTG | GGG | TTT | TTC | 837 |
| Ile | Ile | Gly 230 | Thr | Ile | Tyr | Pro | Ile 235 | Ala | Gly | Tyr | Gly | Leu 240 | Gly | Phe | Phe | |
| CTG | GCT | AGA | ATT | GCT | GGT | CAA | CCC | TGG | TAC | AGG | TGC | CGA | ACA | GTT | GCC | 885 |
| Leu | Ala | Arg 245 | Ile | Ala | Gly | Gln | Pro 250 | Trp | Tyr | Arg | Cys | Arg 255 | Thr | Val | Ala | |
| TTG | GAA | ACC | GGG | TTG | CAG | AAC | ACT | CAG | CTG | TGT | TCC | ACC | ATT | GTG | CAG | 933 |
| Leu 260 | Glu | Thr | Gly | Leu | Gln 265 | Asn | Thr | Gln | Leu | Cys 270 | Ser | Thr | Ile | Val | Gln 275 | |
| CTT | TCC | TTC | AGC | CCT | GAG | GAC | CTC | AAC | CTT | GTG | TTC | ACC | TTC | CCC | CTC | 981 |
| Leu | Ser | Phe | Ser | Pro 280 | Glu | Asp | Leu | Asn | Leu 285 | Val | Phe | Thr | Phe | Pro 290 | Leu | |
| ATC | TAC | AGC | ATC | TTC | CAG | ATC | GCC | TTT | GCA | GCA | ATA | CTA | TTA | GGA | GCT | 1029 |
| Ile | Tyr | Ser | Ile 295 | Phe | Gln | Ile | Ala | Phe 300 | Ala | Ala | Ile | Leu | Leu 305 | Gly | Ala | |
| TAT | GTC | GCA | TAC | AAG | AAA | TGT | CAT | GGA | AAA | AAT | AAT | ACT | GAG | CTA | CAA | 1077 |
| Tyr | Val | Ala 310 | Tyr | Lys | Lys | Cys | His 315 | Gly | Lys | Asn | Asn | Thr 320 | Glu | Leu | Gln | |
| GAG | AAA | ACA | GAC | AAT | GAA | ATG | GAG | CCC | AGG | TCA | TCA | TTT | CAG | GAG | ACA | 1125 |
| Glu | Lys 325 | Thr | Asp | Asn | Glu | Met 330 | Glu | Pro | Arg | Ser | Ser 335 | Phe | Gln | Glu | Thr | |
| AAC | AAA | GGA | TTT | CAA | CCA | GAT | GAG | AAG | TAAAAACTAA | GGGACAGAA | | | | | | 1172 |
| Asn | Lys | Gly | Phe | Gln 345 | Pro | Asp | Glu | Lys | | | | | | | | |
| 340 | | | | | | | | | | | | | | | | |

```
AAGAAAGCTT ACTAACAACA TTCATTAAAC TACAACTATT TCATTGGTG  GAATGATCAG     1232

CAGAAAAAAA TGTTTAAAAT TCAATTCGAA ATTTGTTATT GTTTGGTAC  AAAGTGACTA     1292

GCAATCCATT CTTTATTGTG ACAAACATCT GAGAGAGAGA GAGAGAGATA GAGAGAGAGA    1352

GAGAGAGAGA GAGAGAGAGA GAGAGAGAGA GAGAGAGAGA GTGTGTGTGT GTGTAGAGTG    1412

TGTACATATC CACAGGGGAC TGACTGGTCA CAGGATATCC CTTGATACTA AATTCACAGA    1472

AGCATGAGCT TCTTTCATAA AATGGCAAAA TGTTTGCATT CATCTCTCAT ATACTTCAGA    1532

TCAATACTAA CTTACTTAAA ATATTTAACA TGATGTAAAT GCTATGTAAA TAGTCATTTT    1592

ACTGTATTGT TTAGGAAATG ATGTTTTTTT AAGTCTGTGA TATTTTATGT TCAGTACAGA    1652
```

| | | | | | |
|---|---|---|---|---|---|
| CATCATTTTT | CCTGAAATTT | TTGACAAAAG | TGGGACTTAT | CCATAGAGTT | CAAACTTATT | 1712 |
| CTTGGGAGGA | AAACTGAATT | TACATAGATA | GATATGATCA | ATCATCACTA | ATATATTATC | 1772 |
| AGAAAATATC | TAAAGACCTA | ACTGAATGTA | GATCAGACTG | GAAACCTTGT | TATAGTATGC | 1832 |
| TGAATTCAGA | AACAAGCACT | TTTATATGTT | AAAATATAAC | AGATTATTAT | TATAAAATGT | 1892 |
| TGATTTTCTT | CAGTATTTAT | GATTGTAAAA | AGATGTGAAT | GAATGTATTC | CTTTAATATT | 1952 |
| TTAATCATCA | GTTGAGACT | CTGCAACCTA | TTTATTGTG | ATGTTACAC | TATACTCTGT | 2012 |
| CAAGTGTCTG | TCTTTTACT | TTAGAAAAGT | GGCTTCTTTC | AGTGATATTC | CAAAAGCAGA | 2072 |
| AGTGAGATAA | AGATTACTAA | TGAATTCAAT | AACAAATCAG | AATTGAGTTA | AACTCACCAC | 2132 |
| GGATATTTTA | CATCCGTTCA | CATACTTCTA | TGGTCCACCA | ATGACCACTA | TATCTTTCAA | 2192 |
| GGAAAAGACC | TCATTAGAAC | AGTTTATATC | TGGCAACTTA | GTTGTTGAA | CTCTAGAGAT | 2252 |
| GTTTACTAAA G | | | | | | 2263 |

( 2 ) INFORMATION FOR SEQ ID NO:2:

( i ) SEQUENCE CHARACTERISTICS:
        ( A ) LENGTH: 348 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Asp Asn Ser Ser Ile Cys Asn Pro Asn Ala Thr Ile Cys Glu Gly
 1               5                  10                  15
Asp Ser Cys Ile Ala Pro Glu Ser Asn Phe Asn Ala Ile Leu Ser Val
                20                  25                  30
Val Met Ser Thr Val Leu Thr Ile Leu Leu Ala Leu Val Met Phe Ser
             35                  40                  45
Met Gly Cys Asn Val Glu Leu His Lys Phe Leu Gly His Leu Arg Arg
     50                  55                  60
Pro Trp Gly Ile Val Val Gly Phe Leu Cys Gln Phe Gly Ile Met Pro
 65                  70                  75                  80
Leu Thr Gly Phe Val Leu Ser Val Ala Phe Gly Ile Leu Pro Val Gln
                 85                  90                  95
Ala Val Val Val Leu Ile Gln Gly Cys Cys Pro Gly Gly Thr Ala Ser
                100                 105                 110
Asn Ile Leu Ala Tyr Trp Val Asp Gly Asp Met Asp Leu Ser Val Ser
             115                 120                 125
Met Thr Thr Cys Ser Thr Leu Leu Ala Leu Gly Met Met Pro Leu Cys
     130                 135                 140
Leu Phe Ile Tyr Thr Lys Met Trp Val Asp Ser Gly Thr Ile Val Ile
145                 150                 155                 160
Pro Tyr Asp Ser Ile Gly Thr Ser Leu Val Ala Leu Val Ile Pro Val
                165                 170                 175
Ser Ile Gly Met Tyr Val Asn His Lys Trp Pro Gln Lys Ala Lys Ile
             180                 185                 190
Ile Leu Lys Ile Gly Ser Ile Ala Gly Ala Ile Leu Ile Val Leu Ile
     195                 200                 205
Ala Val Val Gly Gly Ile Leu Tyr Gln Ser Ala Trp Thr Ile Glu Pro
     210                 215                 220
Lys Leu Trp Ile Ile Gly Thr Ile Tyr Pro Ile Ala Gly Tyr Gly Leu
225                 230                 235                 240
```

```
Gly  Phe  Phe  Leu  Ala  Arg  Ile  Ala  Gly  Gln  Pro  Trp  Tyr  Arg  Cys  Arg
               245                      250                      255

Thr  Val  Ala  Leu  Glu  Thr  Gly  Leu  Gln  Asn  Thr  Gln  Leu  Cys  Ser  Thr
               260                      265                      270

Ile  Val  Gln  Leu  Ser  Phe  Ser  Pro  Glu  Asp  Leu  Asn  Leu  Val  Phe  Thr
          275                      280                      285

Phe  Pro  Leu  Ile  Tyr  Ser  Ile  Phe  Gln  Ile  Ala  Phe  Ala  Ala  Ile  Leu
     290                      295                      300

Leu  Gly  Ala  Tyr  Val  Ala  Tyr  Lys  Lys  Cys  His  Gly  Lys  Asn  Asn  Thr
305                      310                      315                      320

Glu  Leu  Gln  Glu  Lys  Thr  Asp  Asn  Glu  Met  Glu  Pro  Arg  Ser  Ser  Phe
               325                      330                      335

Gln  Glu  Thr  Asn  Lys  Gly  Phe  Gln  Pro  Asp  Glu  Lys
               340                      345
```

( 2 ) INFORMATION FOR SEQ ID NO:3:

( i ) SEQUENCE CHARACTERISTICS:
        ( A ) LENGTH: 1047 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1044

( x i ) SEQUENCE DESCRIPTION: SEQ ID NO:3:

```
ATG  AAT  GAT  CCG  AAC  AGC  TGT  GTG  GAC  AAT  GCA  ACA  GTT  TGC  TCT  GGT     48
Met  Asn  Asp  Pro  Asn  Ser  Cys  Val  Asp  Asn  Ala  Thr  Val  Cys  Ser  Gly
  1                 5                        10                      15

GCA  TCC  TGT  GTG  GTA  CCT  GAG  AGC  AAT  TTC  AAT  AAC  ATC  CTA  AGT  GTG     96
Ala  Ser  Cys  Val  Val  Pro  Glu  Ser  Asn  Phe  Asn  Asn  Ile  Leu  Ser  Val
                 20                      25                      30

GTC  CTA  AGT  ACG  GTG  CTG  ACC  ATC  CTG  TTG  GCC  TTG  GTG  ATG  TTC  TCC    144
Val  Leu  Ser  Thr  Val  Leu  Thr  Ile  Leu  Leu  Ala  Leu  Val  Met  Phe  Ser
            35                      40                      45

ATG  GGA  TGC  AAC  GTG  GAA  ATC  AAG  AAA  TTT  CTA  GGG  CAC  ATA  AAG  CGG    192
Met  Gly  Cys  Asn  Val  Glu  Ile  Lys  Lys  Phe  Leu  Gly  His  Ile  Lys  Arg
       50                      55                      60

CCG  TGG  GGC  ATT  TGT  GTT  GGC  TTC  CTC  TGT  CAG  TTT  GGA  ATC  ATG  CCC    240
Pro  Trp  Gly  Ile  Cys  Val  Gly  Phe  Leu  Cys  Gln  Phe  Gly  Ile  Met  Pro
 65                      70                      75                      80

CTC  ACA  GGA  TTC  ATC  CTG  TCG  GTG  GCC  TTT  GAC  ATC  CTC  CCG  CTC  CAG    288
Leu  Thr  Gly  Phe  Ile  Leu  Ser  Val  Ala  Phe  Asp  Ile  Leu  Pro  Leu  Gln
                 85                      90                      95

GCC  GTA  GTG  GTG  CTC  ATT  ATA  GGA  TGC  TGC  CCT  GGA  GGA  ACT  GCC  TCC    336
Ala  Val  Val  Val  Leu  Ile  Ile  Gly  Cys  Cys  Pro  Gly  Gly  Thr  Ala  Ser
            100                     105                     110

AAT  ATC  TTG  GCC  TAT  TGG  GTC  GAT  GGC  GAC  ATG  GAC  CTG  AGC  GTC  AGC    384
Asn  Ile  Leu  Ala  Tyr  Trp  Val  Asp  Gly  Asp  Met  Asp  Leu  Ser  Val  Ser
       115                     120                     125

ATG  ACC  ACA  TGC  TCC  ACA  CTG  CTT  GCC  CTC  GGA  ATG  ATG  CCG  CTG  TGC    432
Met  Thr  Thr  Cys  Ser  Thr  Leu  Leu  Ala  Leu  Gly  Met  Met  Pro  Leu  Cys
 130                     135                     140

CTC  CTT  ATC  TAT  ACC  AAA  ATG  TGG  GTC  GAC  TCT  GGG  AGC  ATC  GTA  ATT    480
Leu  Leu  Ile  Tyr  Thr  Lys  Met  Trp  Val  Asp  Ser  Gly  Ser  Ile  Val  Ile
 145                     150                     155                     160

CCC  TAT  GAT  AAC  ATA  GGT  ACA  TCT  CTG  GTT  GCT  CTC  GTT  GTT  CCT  GTT    528
Pro  Tyr  Asp  Asn  Ile  Gly  Thr  Ser  Leu  Val  Ala  Leu  Val  Val  Pro  Val
```

|  |  |  |  |  |  |  | 165 |  |  |  |  | 170 |  |  |  |  | 175 |  |  |
|---|---|---|---|---|---|---|---|---|---|---|---|---|---|---|---|---|---|---|---|
| TCC | ATT | GGA | ATG | TTT | GTT | AAT | CAC | AAA | TGG | CCC | CAA | AAA | GCA | AAG | ATC |  |  |  | 576 |
| Ser | Ile | Gly | Met<br>180 | Phe | Val | Asn | His | Lys<br>185 | Trp | Pro | Gln | Lys | Ala<br>190 | Lys | Ile |  |  |  |  |
| ATA | CTT | AAA | ATT | GGG | TCC | ATC | GCG | GGC | GCC | ATC | CTC | ATT | GTG | CTC | ATA |  |  |  | 624 |
| Ile | Leu | Lys<br>195 | Ile | Gly | Ser | Ile | Ala<br>200 | Gly | Ala | Ile | Leu | Ile<br>205 | Val | Leu | Ile |  |  |  |  |
| GCT | GTG | GTT | GGA | GGA | ATA | TTG | TAC | CAA | AGC | GCC | TGG | ATC | ATT | GCT | CCC |  |  |  | 672 |
| Ala | Val<br>210 | Val | Gly | Gly | Ile | Leu | Tyr<br>215 | Gln | Ser | Ala | Trp | Ile<br>220 | Ile | Ala | Pro |  |  |  |  |
| AAA | CTG | TGG | ATT | ATA | GGA | ACA | ATA | TTT | CCT | GTG | GCG | GGT | TAC | TCC | CTG |  |  |  | 720 |
| Lys<br>225 | Leu | Trp | Ile | Ile | Gly<br>230 | Thr | Ile | Phe | Pro | Val<br>235 | Ala | Gly | Tyr | Ser | Leu<br>240 |  |  |  |  |
| GGG | TTT | CTT | CTG | GCT | AGA | ATT | GCT | GGT | CTA | CCC | TGG | TAC | AGG | TGC | CGA |  |  |  | 768 |
| Gly | Phe | Leu | Leu | Ala<br>245 | Arg | Ile | Ala | Gly | Leu<br>250 | Pro | Trp | Tyr | Arg | Cys<br>255 | Arg |  |  |  |  |
| ACG | GTT | GCT | TTT | GAA | ACG | GGG | ATG | CAG | AAC | ACG | CAG | CTA | TGT | TCC | ACC |  |  |  | 816 |
| Thr | Val | Ala | Phe<br>260 | Glu | Thr | Gly | Met | Gln<br>265 | Asn | Thr | Gln | Leu | Cys<br>270 | Ser | Thr |  |  |  |  |
| ATC | GTT | CAG | CTC | TCC | TTC | ACT | CCT | GAG | GAG | CTC | AAT | GTC | GTA | TTC | ACC |  |  |  | 864 |
| Ile | Val | Gln<br>275 | Leu | Ser | Phe | Thr | Pro<br>280 | Glu | Glu | Leu | Asn | Val<br>285 | Val | Phe | Thr |  |  |  |  |
| TTC | CCG | CTC | ATC | TAC | AGC | ATT | TTC | CAG | CTC | GCC | TTT | GCC | GCA | ATA | TTC |  |  |  | 912 |
| Phe | Pro<br>290 | Leu | Ile | Tyr | Ser | Ile<br>295 | Phe | Gln | Leu | Ala | Phe<br>300 | Ala | Ala | Ile | Phe |  |  |  |  |
| TTA | GGA | TTT | TAT | GTG | GCA | TAC | AAG | AAA | TGT | CAT | GGA | AAA | AAC | AAG | GCA |  |  |  | 960 |
| Leu<br>305 | Gly | Phe | Tyr | Val | Ala<br>310 | Tyr | Lys | Lys | Cys | His<br>315 | Gly | Lys | Asn | Lys | Ala<br>320 |  |  |  |  |
| GAA | ATT | CCA | GAG | AGC | AAA | GAA | AAT | GGA | ACG | GAG | CCA | GAG | TCA | TCG | TTT |  |  |  | 1008 |
| Glu | Ile | Pro | Glu | Ser<br>325 | Lys | Glu | Asn | Gly | Thr<br>330 | Glu | Pro | Glu | Ser | Ser<br>335 | Phe |  |  |  |  |
| TAT | AAG | GCA | AAT | GGA | GGA | TTT | CAA | CCT | GAC | GAA | AAG | TAG |  |  |  |  |  |  | 1047 |
| Tyr | Lys | Ala | Asn<br>340 | Gly | Gly | Phe | Gln | Pro<br>345 | Asp | Glu | Lys |  |  |  |  |  |  |  |  |

( 2 ) INFORMATION FOR SEQ ID NO:4:

( i ) SEQUENCE CHARACTERISTICS:
        ( A ) LENGTH: 348 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met<br>1 | Asn | Asp | Pro | Asn<br>5 | Ser | Cys | Val | Asp | Asn<br>10 | Ala | Thr | Val | Cys | Ser<br>15 | Gly |
|---|---|---|---|---|---|---|---|---|---|---|---|---|---|---|---|
| Ala | Ser | Cys | Val<br>20 | Val | Pro | Glu | Ser | Asn<br>25 | Phe | Asn | Asn | Ile | Leu<br>30 | Ser | Val |
| Val | Leu | Ser<br>35 | Thr | Val | Leu | Thr | Ile<br>40 | Leu | Leu | Ala | Leu | Val<br>45 | Met | Phe | Ser |
| Met | Gly<br>50 | Cys | Asn | Val | Glu | Ile<br>55 | Lys | Lys | Phe | Leu | Gly<br>60 | His | Ile | Lys | Arg |
| Pro<br>65 | Trp | Gly | Ile | Cys | Val<br>70 | Gly | Phe | Leu | Cys | Gln<br>75 | Phe | Gly | Ile | Met | Pro<br>80 |
| Leu | Thr | Gly | Phe | Ile<br>85 | Leu | Ser | Val | Ala | Phe<br>90 | Asp | Ile | Leu | Pro | Leu<br>95 | Gln |
| Ala | Val | Val | Val<br>100 | Leu | Ile | Ile | Gly | Cys<br>105 | Cys | Pro | Gly | Gly | Thr<br>110 | Ala | Ser |
| Asn | Ile | Leu | Ala | Tyr | Trp | Val | Asp | Gly | Asp | Met | Asp | Leu | Ser | Val | Ser |

|     | 115 |     |     |     |     | 120 |     |     |     |     | 125 |     |     |     |
| --- | --- | --- | --- | --- | --- | --- | --- | --- | --- | --- | --- | --- | --- | --- |
| Met | Thr 130 | Thr | Cys | Ser | Thr | Leu 135 | Leu | Ala | Leu | Gly | Met 140 | Met | Pro | Leu | Cys |
| Leu 145 | Leu | Ile | Tyr | Thr | Lys 150 | Met | Trp | Val | Asp | Ser 155 | Gly | Ser | Ile | Val | Ile 160 |
| Pro | Tyr | Asp | Asn | Ile 165 | Gly | Thr | Ser | Leu | Val 170 | Ala | Leu | Val | Val | Pro 175 | Val |
| Ser | Ile | Gly | Met 180 | Phe | Val | Asn | His | Lys 185 | Trp | Pro | Gln | Lys | Ala 190 | Lys | Ile |
| Ile | Leu | Lys 195 | Ile | Gly | Ser | Ile | Ala 200 | Gly | Ala | Ile | Leu | Ile 205 | Val | Leu | Ile |
| Ala | Val 210 | Val | Gly | Gly | Ile | Leu 215 | Tyr | Gln | Ser | Ala | Trp 220 | Ile | Ile | Ala | Pro |
| Lys 225 | Leu | Trp | Ile | Ile | Gly 230 | Thr | Ile | Phe | Pro | Val 235 | Ala | Gly | Tyr | Ser | Leu 240 |
| Gly | Phe | Leu | Leu | Ala 245 | Arg | Ile | Ala | Gly | Leu 250 | Pro | Trp | Tyr | Arg | Cys 255 | Arg |
| Thr | Val | Ala | Phe 260 | Glu | Thr | Gly | Met | Gln 265 | Asn | Thr | Gln | Leu | Cys 270 | Ser | Thr |
| Ile | Val | Gln 275 | Leu | Ser | Phe | Thr | Pro 280 | Glu | Glu | Leu | Asn | Val 285 | Val | Phe | Thr |
| Phe | Pro 290 | Leu | Ile | Tyr | Ser | Ile 295 | Phe | Gln | Leu | Ala | Phe 300 | Ala | Ala | Ile | Phe |
| Leu 305 | Gly | Phe | Tyr | Val | Ala 310 | Tyr | Lys | Lys | Cys | His 315 | Gly | Lys | Asn | Lys | Ala 320 |
| Glu | Ile | Pro | Glu | Ser 325 | Lys | Glu | Asn | Gly | Thr 330 | Glu | Pro | Glu | Ser | Ser 335 | Phe |
| Tyr | Lys | Ala | Asn 340 | Gly | Gly | Phe | Gln | Pro 345 | Asp | Glu | Lys |     |     |     |     |

( 2 ) INFORMATION FOR SEQ ID NO:5:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

| Ser 1 | Phe | Gln | Glu | Thr 5 | Asn | Lys | Gly | Phe | Gln 10 | Pro | Asp | Glu | Lys |